United States Patent
Chuang et al.

(10) Patent No.: US 9,768,577 B2
(45) Date of Patent: Sep. 19, 2017

(54) SEMICONDUCTOR INSPECTION AND METROLOGY SYSTEM USING LASER PULSE MULTIPLIER

(71) Applicant: KLA-Tencor Corporation, Milpitas, CA (US)

(72) Inventors: Yung-Ho Alex Chuang, Cupertino, CA (US); Justin Dianhuan Liou, Santa Clara, CA (US); J. Joseph Armstrong, Fremont, CA (US); Yujun Deng, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 77 days.

(21) Appl. No.: 14/832,833

(22) Filed: Aug. 21, 2015

(65) Prior Publication Data
US 2015/0364895 A1 Dec. 17, 2015

Related U.S. Application Data

(62) Division of application No. 13/711,593, filed on Dec. 11, 2012, now Pat. No. 9,151,940.
(Continued)

(51) Int. Cl.
*H01S 3/00* (2006.01)
*G02B 17/00* (2006.01)
(Continued)

(52) U.S. Cl.
CPC .............. *H01S 3/005* (2013.01); *C23C 16/00* (2013.01); *G02B 17/00* (2013.01);
(Continued)

(58) Field of Classification Search
CPC ... H01S 3/005; H01S 3/00; H01S 3/10; C23C 16/00; G02B 17/00; G02B 17/0848; G02B 27/00; G02B 27/108; G02B 27/14
(Continued)

(56) References Cited

U.S. PATENT DOCUMENTS 3,755,704 A 8/1973 Spindt et al.
4,467,189 A 8/1984 Tsuchiya
(Continued)

FOREIGN PATENT DOCUMENTS

EP 0746871 B1 5/2000
EP 0602983 B1 6/2000
(Continued)

OTHER PUBLICATIONS

KLA-Tencor Corporation; PCT International Search Report dated Dec. 29, 2015 for Application No. PCT/US2015/051538, 3 pages.
(Continued)

*Primary Examiner* — William R Alexander
(74) *Attorney, Agent, or Firm* — Bever, Hoffman & Harms, LLP

(57) ABSTRACT

A pulse multiplier includes a beam splitter and one or more mirrors. The beam splitter receives a series of input laser pulses and directs part of the energy of each pulse into a ring cavity. After circulating around the ring cavity, part of the pulse energy leaves the ring cavity through the beam splitter and part of the energy is recirculated. By selecting the ring cavity optical path length, the repetition rate of an output series of laser pulses can be made to be a multiple of the input repetition rate. The relative energies of the output pulses can be controlled by choosing the transmission and reflection coefficients of the beam splitter. This pulse multiplier can inexpensively reduce the peak power per pulse while increasing the number of pulses per second with minimal total power loss.

21 Claims, 15 Drawing Sheets

Related U.S. Application Data

(60) Provisional application No. 61/733,858, filed on Dec. 5, 2012.

(51) Int. Cl.
*G02B 27/00* (2006.01)
*C23C 16/00* (2006.01)
*G02B 17/08* (2006.01)
*G02B 27/10* (2006.01)
*H01S 3/10* (2006.01)

(52) U.S. Cl.
CPC ......... *G02B 17/0848* (2013.01); *G02B 27/00* (2013.01); *G02B 27/108* (2013.01); *H01S 3/00* (2013.01); *H01S 3/10* (2013.01)

(58) Field of Classification Search
USPC .................. 359/638, 629, 618, 639, 640
See application file for complete search history.

(56) References Cited

U.S. PATENT DOCUMENTS

| | | | |
|---|---|---|---|
| 4,644,221 A | 2/1987 | Gutierrez et al. | |
| 4,710,030 A | 12/1987 | Tauc et al. | |
| 4,718,766 A | 1/1988 | Greenstein | |
| 4,853,595 A | 8/1989 | Alfano et al. | |
| 4,999,014 A | 3/1991 | Gold et al. | |
| 5,119,382 A | 6/1992 | Kennedy et al. | |
| 5,120,949 A | 6/1992 | Tomasetti | |
| 5,144,630 A | 9/1992 | Lin | |
| 5,172,382 A | 12/1992 | Loh et al. | |
| 5,189,481 A | 2/1993 | Jann et al. | |
| 5,276,548 A | 1/1994 | Margalith | |
| 5,309,456 A * | 5/1994 | Horton ................. | H01S 3/0057 372/25 |
| 5,563,702 A | 10/1996 | Emery et al. | |
| 5,742,626 A | 4/1998 | Mead et al. | |
| 5,760,809 A | 6/1998 | Malhotra et al. | |
| 5,760,899 A | 6/1998 | Eismann | |
| 5,999,310 A | 12/1999 | Shafer et al. | |
| 6,064,759 A | 5/2000 | Buckley et al. | |
| 6,191,887 B1 | 2/2001 | Michaloski et al. | |
| 6,201,601 B1 | 3/2001 | Vaez-Iravani et al. | |
| 6,233,052 B1 | 5/2001 | Zare et al. | |
| 6,271,916 B1 | 8/2001 | Marxer et al. | |
| 6,275,514 B1 | 8/2001 | Katzir | |
| 6,285,018 B1 | 9/2001 | Aebi et al. | |
| 6,373,869 B1 | 4/2002 | Jacob | |
| 6,535,531 B1 * | 3/2003 | Smith .................. | G03F 7/7055 372/25 |
| 6,549,267 B1 | 4/2003 | Kudo | |
| 6,577,782 B1 | 6/2003 | Leaird et al. | |
| 6,608,676 B1 | 8/2003 | Zhao et al. | |
| 6,693,930 B1 | 2/2004 | Chuang et al. | |
| 6,734,968 B1 | 5/2004 | Wang et al. | |
| 6,816,520 B1 | 11/2004 | Tulloch et al. | |
| 7,151,632 B2 | 12/2006 | Biss et al. | |
| 7,187,500 B2 | 3/2007 | Chuang et al. | |
| 7,313,155 B1 | 12/2007 | Mu | |
| 7,321,468 B2 * | 1/2008 | Herkommer ......... | G02B 27/126 359/618 |
| 7,352,457 B2 | 4/2008 | Kvamme et al. | |
| 7,432,517 B2 * | 10/2008 | Botma ............... | B23K 26/0613 250/493.1 |
| 7,449,673 B2 | 11/2008 | Chuang et al. | |
| 7,525,649 B1 | 4/2009 | Leong et al. | |
| 7,528,342 B2 | 5/2009 | Deshi | |
| 7,528,943 B2 | 5/2009 | Brown et al. | |
| 7,586,108 B2 | 9/2009 | Nihtianov et al. | |
| 7,609,309 B2 | 10/2009 | Brown et al. | |
| 7,667,841 B2 | 2/2010 | Opsal | |
| 7,813,406 B1 * | 10/2010 | Nguyen ............. | B23K 26/0622 356/300 |
| 7,875,948 B2 | 1/2011 | Hynecek et al. | |
| 7,952,633 B2 | 5/2011 | Brown et al. | |
| 7,999,342 B2 | 8/2011 | Hsu et al. | |
| 8,309,443 B2 | 11/2012 | Tanaka et al. | |
| 8,514,587 B2 | 8/2013 | Zhang et al. | |
| 8,618,254 B2 | 12/2013 | Giaccia et al. | |
| 8,629,384 B1 | 1/2014 | Biellak et al. | |
| 8,686,331 B2 | 4/2014 | Armstrong | |
| 8,755,417 B1 | 6/2014 | Dribinski | |
| 8,873,596 B2 | 10/2014 | Dribinski | |
| 8,891,079 B2 | 11/2014 | Zhao et al. | |
| 8,929,406 B2 | 1/2015 | Chuang et al. | |
| 2002/0191834 A1 | 12/2002 | Fishbaine | |
| 2003/0043876 A1 | 3/2003 | Lublin et al. | |
| 2004/0095573 A1 | 5/2004 | Tsai et al. | |
| 2005/0110988 A1 | 5/2005 | Nishiyama et al. | |
| 2005/0122021 A1 | 6/2005 | Smith et al. | |
| 2005/0190452 A1 | 9/2005 | Govorkov et al. | |
| 2006/0126681 A1 | 6/2006 | Botma et al. | |
| 2006/0126682 A1 | 6/2006 | Rodin et al. | |
| 2006/0171036 A1 | 8/2006 | Govorkov et al. | |
| 2007/0002465 A1 | 1/2007 | Chuang et al. | |
| 2007/0047600 A1 | 3/2007 | Luo et al. | |
| 2007/0090278 A1 | 4/2007 | Botma | |
| 2007/0096648 A1 | 5/2007 | Nakajima et al. | |
| 2007/0103769 A1 | 5/2007 | Kuwabara | |
| 2007/0121107 A1 | 5/2007 | Tsai et al. | |
| 2007/0188744 A1 | 8/2007 | Leslie et al. | |
| 2007/0291810 A1 | 12/2007 | Luo et al. | |
| 2007/0295974 A1 | 12/2007 | Fontanella | |
| 2008/0182092 A1 | 7/2008 | Bondokov et al. | |
| 2008/0267241 A1 | 10/2008 | Brown | |
| 2009/0052480 A1 | 2/2009 | Cobb et al. | |
| 2009/0080085 A1 | 3/2009 | Botma | |
| 2009/0108207 A1 | 4/2009 | Liu | |
| 2009/0128912 A1 | 5/2009 | Okada | |
| 2009/0180176 A1 | 7/2009 | Armstrong et al. | |
| 2010/0103409 A1 | 4/2010 | Ohshima et al. | |
| 2010/0108913 A1 | 5/2010 | Ershov et al. | |
| 2010/0163757 A1 | 7/2010 | Joobeur et al. | |
| 2010/0188655 A1 | 7/2010 | Brown et al. | |
| 2010/0301437 A1 | 12/2010 | Brown et al. | |
| 2011/0073982 A1 | 3/2011 | Armstrong et al. | |
| 2011/0101219 A1 | 5/2011 | Uchiyama et al. | |
| 2011/0228263 A1 | 9/2011 | Chuang et al. | |
| 2011/0279819 A1 | 11/2011 | Chuang et al. | |
| 2012/0026578 A1 | 2/2012 | Sakuma | |
| 2012/0160993 A1 | 6/2012 | Nevet et al. | |
| 2012/0314286 A1 * | 12/2012 | Chuang ................ | G02B 27/281 359/489.08 |
| 2013/0009069 A1 | 1/2013 | Okada | |
| 2013/0016346 A1 | 1/2013 | Romanovsky et al. | |
| 2013/0020491 A1 | 1/2013 | Mazzillo | |
| 2013/0077086 A1 | 3/2013 | Chuang et al. | |
| 2013/0082241 A1 | 4/2013 | Kub et al. | |
| 2013/0088706 A1 | 4/2013 | Chuang et al. | |
| 2013/0126705 A1 | 5/2013 | Maleev | |
| 2013/0169957 A1 | 7/2013 | Wolf et al. | |
| 2013/0176552 A1 | 7/2013 | Brown et al. | |
| 2013/0194445 A1 | 8/2013 | Brown et al. | |
| 2013/0264481 A1 | 10/2013 | Chern et al. | |
| 2013/0313440 A1 | 11/2013 | Chuang et al. | |
| 2013/0336574 A1 | 12/2013 | Nasser-Ghodsi et al. | |
| 2014/0016655 A1 | 1/2014 | Armstrong | |
| 2014/0034816 A1 | 2/2014 | Chuang et al. | |
| 2014/0050234 A1 | 2/2014 | Ter-Mikirtychev | |
| 2014/0111799 A1 | 4/2014 | Lei et al. | |
| 2014/0153596 A1 * | 6/2014 | Chuang ................ | G02B 17/00 372/25 |
| 2014/0158864 A1 | 6/2014 | Brown et al. | |
| 2014/0204963 A1 | 7/2014 | Chuang et al. | |
| 2014/0226140 A1 | 8/2014 | Chuang et al. | |
| 2014/0291493 A1 | 10/2014 | Chuang et al. | |
| 2014/0305367 A1 | 10/2014 | Chuang et al. | |
| 2015/0007765 A1 | 1/2015 | Dribinski | |
| 2015/0041666 A1 | 2/2015 | Chuang et al. | |
| 2015/0177159 A1 | 6/2015 | Brown et al. | |
| 2015/0200216 A1 | 7/2015 | Muramatsu et al. | |

(56) References Cited

U.S. PATENT DOCUMENTS

| | | |
|---|---|---|
| 2015/0275393 A1 | 10/2015 | Bondokov et al. |
| 2015/0294998 A1 | 10/2015 | Nihtianov |
| 2015/0372446 A1 | 12/2015 | Chuang et al. |

FOREIGN PATENT DOCUMENTS

| | | |
|---|---|---|
| EP | 1939917 A2 | 7/2008 |
| JP | H0511287 A | 1/1993 |
| JP | 2003043533 A | 2/2003 |
| JP | 2005148550 A | 6/2005 |
| JP | 2006-186046 A | 7/2006 |
| JP | 200786108 | 4/2007 |
| JP | 2007085958 A | 4/2007 |
| JP | 2007511908 A | 5/2007 |
| JP | 2007249092 A | 9/2007 |
| JP | 2007298932 A | 11/2007 |
| JP | 2009076906 A | 4/2009 |
| JP | 2010003755 A | 1/2010 |
| JP | 4627185 B2 | 2/2011 |
| JP | 2012-098103 A | 5/2012 |
| KR | 10-2000-0034461 A | 6/2000 |
| KR | 1020100025297 A | 3/2010 |
| WO | 9532518 A1 | 11/1995 |
| WO | 9617372 A1 | 6/1996 |
| WO | 00/14834 A1 | 3/2000 |
| WO | WO2010/037106 A2 | 4/2010 |
| WO | 2010037106 A3 | 6/2010 |
| WO | 2011041472 A1 | 4/2011 |
| WO | 2011/064059 A1 | 6/2011 |
| WO | 2012091786 A1 | 7/2012 |
| WO | 2014067754 A2 | 5/2014 |

OTHER PUBLICATIONS

Armstrong, Carter M.The Quest for the Ultimate Vacuum Tube, Spectrum IEEE, Dec. 2015, 4 pgs.

Ding, MengField Emission from Silicon, MIT 2001, 277 pgs.

Fanton et al, Multiparameter Measurements of Thin Film . . . , Journal of Applied Physics, vol. 73, No. 11, p. 7035 (1993).

Field Emitter Review, 7 pgs in Japanese.

Fowler, R. H., et al, Electron Emission in Intense Electric Fields, Mar. 31, 1928, 9 pgs.

Koike, AkifumiField Emitter Equipped With a Suppressor to Control Emission Angel, IEEE Electron Device Letters, vol. 34, No. 5, May 2013, 3 pgs.

Nagao, Masayoshi, Cathode Technologies for Field Emission Displays, IEEJ Trans 2006; 1:171-178, 8 pgs.

Nagao, MasayoshiFabrication of a Field Emitter Array with a Built-In Einzel Lens, JJAP 48 (2008) 06FK02, 4 pgs.

Neo, YoichiroElectron Optical Properties of Microcolumn with Field Emitter, JJAP 52 (2013) 036603, 5 pgs.

Rakhshandehroo, M.R. et al, Fabrication of a self-aligned silicon field emission . . . , JVSTB, 16, 765 (1998); doi: 10.1116/1,589900, 6 pgs.

Rakhshandehroo, M.R. et al, Field emission from gated Si emitter tips with precise . . . , JVSTB, 15, 2777 (1997); doi: 10.1116/1. 589726, 6 pgs.

Sato, T., et al, Fabrication and characterization of HfC coated . . . , J. Vac. Sci. Technol. B 2194), published Jul. 31, 2003, 5 pgs.

Serbun Pavel et al, Stable field emission of single B-doped . . . , JVSTB, 31, 02B101 (2013); doi: 10.1116/1.4765088, 7 pgs.

Utsumi, TakaoVacuum Microelectrnoics: What's New and Exciting, IEEE vol. 38, No. 10, Oct. 1991, 8 pgs.

Huang, Qiyu et al., "Back-Side Illuminated Photogate CMOS Active Pixel Sensor Structure With Improved Short Wavelength Response", IEEE Sensors Journal, vol. 11, No. 9, Sep. 2011, 5 pages.

Itzler, Mark et al., "InP-based Geiger-mode avalanche photodiode arrays for three-dimensional imaging at 1.06 μm", Proceedings of SPIE, vol. 7320 (2000), 12 pages.

Niclass, Cristiano et al., "Design and Characterization of a CMOS 3-D Image Sensor Based on Single Photon Avalanche Diodes", IEEE Journal of Solid-State Circuits, vol. 40, No. 9, Sep. 2005, 8 pages.

Paetzel, Rainer et al., "Activation of Silicon Wafer by Excimer Laser" 18th IEEE Conf. Advanced Thermal processing of Semiconductors—RTP 2010, 5 pages.

Stevanovic, Nenad et al., "A CMOS Image Sensor for High-Speed Imaging", 2000 IEEE Int'l. Conference Solid-State Circuits, 3 pages.

Dulinski, Wojciech et al., "Tests of a backside illuminated monolithic CMOS pixel sensor in an HPD set-up", Nuclear Instruments and Methods in Physics Research A 546 (2005) 274-280, 7 pages.

Sarubbi, F et al, "Pure boron-doped photodiodes: a solution for radiation detection in EUV lithography", Proceedings of the 38th EP Solid-State Device Research Conf., Edinburgh Int'l. Conf. Centre, Endiburgh, Scotland, UK, Sep. 15-19, 2008, Piscataway, NJ: IEEE, US, pp. 278-281.

Fu, Xiaoqian, "Higher Quantum Efficiency by Optimizing GaN Photocathode Structure", 978-1-4244-6644-3/10/ © 2010 IEEE, pp. 234-235.

Sakic, Agata, "Boron-layer silicon photodiodes for high-efficiency low-energy electron detection", Solid-State Electronics 65-66 (2011), pp. 38-44.

Omatsu, Takashige et al., "High repetition rate Q-switching performance in transversely diode-pumped Nd doped mixed gadolinium yttrium vanadate bounce laser", Optics Express vol. 14, Issue 7, pp. 2727-2734, Apr. 3, 2006.

KLA-Tencor Corporation, filed U.S. Appl. No. 14/248,045, filed Apr. 8, 2014 and entitled "Passivation of Nonlinear Optical Crystals".

KLA-Tencor Corporation, filed U.S. Appl. No. 62/059,368, filed Oct. 3, 2014 and entitled "183nm Laser and Inspection System".

KLA-Tencor Corpoation, filed U.S. Appl. No. 14/210,355, filed Mar. 13, 2014 and entitled "193nm Laser and an Inspection System Using a 193nm Laser".

Raoult, F. et al., "Efficient generation of narrow-bandwidth picosecond pulses by frequency doubling of femtosecond chirped pulses", Jul. 15, 1998 / ol. 23, No. 14 / Optics Letters, pp. 1117-1119.

Herriott et al.: "Off-Axis Paths in Spherical Mirror Interferometers", Applied Optics 3, #4, pp. 523-526 (1964).

Herriott et al.: "Folded Optical Delay Lines", Applied Optics 4, #8, pp. 883-889 (1965).

White, John U.: "Long Optical Paths of Large Aperture", Journal of the Optical Society of America 32, #5, pp. 285-288 (1942).

International Search Report and Written Opinion dated Mar. 19, 2014 for PCT/US2013/072774 filed Dec. 3, 2013 in the name of KLA-Tencor Corporation (14 pages).

\* cited by examiner

SEMICONDUCTOR INSPECTION AND METROLOGY SYSTEM USING LASER PULSE MULTIPLIER

RELATED APPLICATIONS

This application is a divisional of U.S. patent application Ser. No. 13/711,593, entitled "Semiconductor Inspection And Metrology System Using Laser Pulse Multiplier" filed Dec. 11, 2012, which claims priority to U.S. Provisional Patent Application 61/733,858, entitled "Semiconductor Inspection And Metrology System Using Laser Pulse Multiplier" filed Dec. 5, 2012, and is related to U.S. Provisional Patent Application 61/496,446, entitled "Optical Peak Power Reduction Of Laser Pulses And Semiconductor Inspection And Metrology Systems Using Same" filed Jun. 13, 2011, and to U.S. application Ser. No. 13/487,075, entitled "Semiconductor Inspection And Metrology System Using Laser Pulse Multiplier" filed Jun. 1, 2012. All of these applications are incorporated by reference herein.

BACKGROUND OF THE INVENTION

Field of the Invention

The present invention relates to using optical peak power reduction of laser pulses for semiconductor inspection and metrology systems, and in particular to using a beam splitter and one or more mirrors to generate an optimized pulse multiplier.

Related Art

The illumination needs for inspection and metrology are generally best met by continuous wave (CW) light sources. A CW light source has a constant power level, which allows for images or data to be acquired continuously. However, at many wavelengths of interest, particularly ultraviolet (UV) wavelengths, CW light sources of sufficient radiance (power per unit area per unit solid angle) are not available, are expensive or are unreliable.

A pulsed light source has an instantaneous peak power level much higher than the time-averaged power level of a CW light source. However, if a pulsed laser is the only available, or cost-effective, light source with sufficient time-averaged radiance at the wavelength of interest, then using a laser with a high repetition rate and wide pulse width is best. The higher the pulse repetition rate, the lower the instantaneous peak power per pulse for the same time-averaged power level. The lower peak power of the laser pulses results in less damage to the optics and to the sample or wafer being measured, as most damage mechanisms are non-linear and depend more strongly on peak power rather than on average power.

In some applications, an additional advantage of an increased repetition rate is that more pulses are collected per data acquisition or per pixel leading to better averaging of the pulse-to-pulse variations and better signal-to-noise ratios. Furthermore, for a rapidly moving sample, a higher pulse rate may lead to a better sampling of the sample position as a function of time, as the distance moved between each pulse is smaller.

The repetition rate of a laser subsystem can be increased by improving the laser medium, the pump system, and/or its driving electronics. Unfortunately, modifying a UV laser that is already operating at a predetermined repetition rate can require a significant investment of time and money to improve one or more of its constituent elements, and may only improve the repetition rate by a small increment. Furthermore increasing the repetition rate of the fundamental laser in a UV laser reduces the peak power of the fundamental. This reduces the efficiency of the frequency conversion (which is necessarily a non-linear process) and so makes it harder to generate high average UV power levels.

Therefore, a need arises for a practical, inexpensive technique to improve the repetition rate of a UV laser that operates on the output of the laser.

SUMMARY OF THE INVENTION

In general, a method of generating optimized pulses for a system is described. In this method, an input laser pulse can be optically split into a plurality of pulses using a beam splitter and a ring cavity. An incoming pulse is split into two by a beam splitter. Part of the pulse continues on, and part of the pulse enters the ring cavity. After the pulse travels once around the ring cavity, it re-encounters the beam splitter and is again split into two. One part leaves the ring cavity, and the other part travels again around the ring cavity.

If the laser generates a stream of pulses substantially equally separated in time (i.e. the pulses are generated at a substantially constant repetition rate), then the ring cavity length can be set so that a pulse that has traveled once around the cavity will arrive in between incoming laser pulses. For example, the ring cavity length can be set so that a pulse that travels once around the ring cavity in approximately half the time interval between two incoming pulses.

The beam splitter determines what fraction of the energy of each incident pulse enters the ring cavity. The beam splitter also determines what fraction of the energy of a pulse that has traveled around the cavity will leave the cavity. By appropriate choice of beam splitter, the relative amplitudes of the pulses can be controlled. In one embodiment, the ring cavity length is chosen so that a pulse travels around the ring cavity in approximately half the time interval between two incoming pulses, and the beam splitter is chosen so that the pulses that leave the ring cavity are approximately equal to one another in energy, thereby effectively doubling the repetition rate of the laser.

A pulse multiplier can include a beam splitter, and a set of mirrors. The beam splitter receives an input laser pulse. The set of mirrors create the ring cavity. In some embodiments, the ring cavity includes a prism so that the prism and mirrors together create the cavity. The beam splitter advantageously reflects (or transmits) the first set of pulses as an output of the pulse multiplier and transmits (or reflects) the second set of pulses back into the ring cavity.

One or more of the mirrors in cavity may be curved in order to refocus the pulses in the ring cavity. In some embodiments, one or more lenses can be incorporated into the cavity to refocus the pulses.

In one embodiment, the output of one cavity may be directed to the input of another cavity. In one embodiment, the first ring cavity can generate a stream of pulses at twice the rate of the repetition rate of the laser, and the second ring cavity can double the repetition rate again, thereby multiplying the laser repetition rate by four. In some embodiments, three ring cavities may be used to multiply the repetition rate by eight, or four ring cavities may be used to multiply the repetition rate by 16.

Any of the above-described pulse multipliers can be incorporated into a wafer inspection system, a patterned wafer system, a mask inspection system, or a metrology system. The pulse multiplier can inexpensively reduce the peak power per pulse while increasing the number of pulses per second with minimal total power loss. The pulse multiplier can advantageously enable high speed inspection and metrology with off-the-shelf lasers.

DETAILED DESCRIPTION OF THE DRAWINGS

In accordance with one aspect of an improved pulse multiplier, each laser pulse can be optically split into a plurality of pulses. In one embodiment, these pulses may be of approximately equal energy and may be approximately equally spaced in time. This splitting of the laser pulse can provide a practical and inexpensive solution to the above-noted problems with minimal energy losses.

Figure 1A:
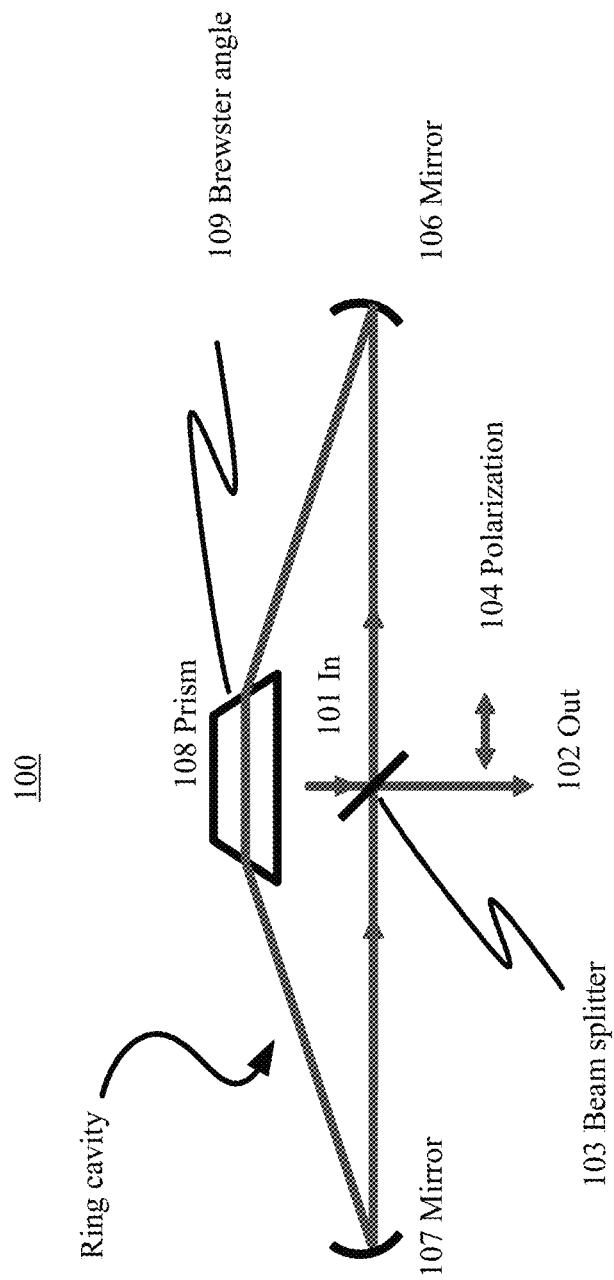
FIG. 1A illustrates an exemplary pulse multiplier configured to generate a pulse train with a repetition rate that is an integer multiple of the rate of an input pulse train.

FIG. 1A illustrates an exemplary pulse multiplier 100 configured to generate pulse trains from each input pulse. Input pulses arrive from direction 101 and impinge on a beam splitter 103, which transmits part of each pulse in an output direction 102, and reflects part to a mirror 106. The input and output pulses are substantially polarized in a direction parallel to arrow 104. Thus, the output polarization is substantially parallel to the input polarization.

The mirror 106 directs the light of the input pulse to a prism 108. Light leaving the prism 108 is directed to a mirror 107, which directs the light back to the beam splitter 103. Hence, the two mirrors 106 and 107, the prism 108, and the beam splitter 103 form a ring cavity. Part of each pulse arriving at the beam splitter 103 from the mirror 107 is reflected out of the ring cavity, and part is transmitted through the beam splitter 103 and recirculates around the ring cavity. The beam splitter 103 is described in more detail later.

The mirrors 106 and 107 have radii of curvature (and hence focal lengths) chosen so that they refocus the light within the cavity, in order to substantially or partly preserve the laser beam waist size and shape for, at least, a few round trips around the ring cavity. For example, but not by way of limitation, the input laser pulses may be substantially collimated, the mirror 106 may focus each laser pulse to a beam waist near the center of the prism 108, and the mirror 107 may substantially re-collimate each laser pulse. This arrangement has the advantage of not having a beam waist on, or near, the beam splitter 103 and hence not subjecting the beam splitter 103 to the highest power densities. One of skill in the appropriate arts would understand that many other focusing arrangements are possible.

The input face 109 of the prism 108 is preferably cut so that the light is incident at an angle substantially or approximately equal to Brewster's angle for the material of the prism, thereby minimizing light losses due to reflection from the input face 109. Preferably the output face (not labeled) is also oriented at Brewster's angle to minimize light losses at the output face. Because the input light pulses are substantially polarized in direction 104, the use of Brewster's angle for both prism faces substantially eliminates light loss due to the prism 108. In some preferred embodiments, the prism 108 may comprise ultraviolet (UV)-grade or excimer-grade fused silica, calcium fluoride ($CaF_2$) or magnesium fluoride ($MgF_2$).

In preferred embodiments, the optical path length of the ring cavity is set to be substantially or approximately equal to a unit fraction of the distance between successive incoming pulses, where the distance between two pulses is equal to the velocity of light multiplied by the time interval between those pulses. For example, in some embodiments the optical path length of the cavity may be set to be substantially or approximately one half, one third, or one quarter of the distance between the incoming pulses. For such ring cavities, every second, third, or fourth pulse, respectively, will substantially or approximately coincide with an arriving input pulse. By way of example, but not limitation, if the incoming laser pulses have a repetition rate of 125 MHz, then a ring cavity optical path length of 1.199 m would generate pulses that are alternately substantially mid-way between two incoming pulses and approximately coincident with an incoming pulse, thus generating output pulses at a repetition rate of 250 MHz.

In some embodiments, the cavity optical path length may be set to an appropriate multiple of the unit fraction of the distance between successive incoming pulses. For example, in a pulse doubler, the ring cavity optical path length may be set to be substantially or approximately 3/2 or 5/2 times the distance between successive incoming pulses, instead of one half of the distance. This length can be advantageous when the output repetition rate is high, for example about 1 GHz or higher, because the required physical cavity length would only be 15 cm or shorter (depending on the repetition rate and the number of reflections from mirrors). Such a short ring cavity length may be difficult to align, or may require too large an angle of incidence on one of more of the curved mirrors in order to accommodate a laser beam waist of 1 mm or a few mm. Generally, it is preferred to keep the angles of incidence on the curved mirrors small in order to keep optical aberrations small.

The ring cavity optical path length may be slightly greater than, or slightly less than, the nominal length calculated directly from the pulse interval divided by the multiplication factor. This length results in the pulses not arriving at exactly the same time at the beam splitter and slightly broadening the output pulse. For example, but not by way of limitation, when the input pulse repetition rate is 125 MHz and the input pulse width is approximately 100 ps, the nominal ring cavity delay would be 4 ns for frequency multiplication by 2 (i.e. a cavity optical path length of about 1.199 m). In one embodiment, a ring cavity optical path length corresponding to 4.05 ns (i.e. a ring cavity optical path length of about 1.214 m) can be used so that the multiplied reflected pulses only slightly overlap with each other or with incoming pulses. In this way, the 4.05 ns cavity length for the 125 MHz input pulse repetition rate can advantageously broaden the pulse and reduce the pulse height. Other pulse multipliers having different input pulse rates or multiplication factors can have different cavity delays. Note that, in this example, a cavity optical path length corresponding to about 3.95 ns would achieve a substantially similar reduction in height of the output pulse.

Note that laser pulses do not typically have sharp rise and fall times, and in many cases have an approximately a Gaussian shape. For the purposes of choosing the appropriate ring cavity length so as to reduce the peak power, the pulse width may be defined as the full width at half maximum (FWHM) of the pulse, or the $1/e^2$ width or any other measure of the pulse width. In some preferred embodiments, the cavity optical path length may be set to be longer or shorter than the equivalent of half the interval between successive pulses by an amount approximately equal to about half the pulse width.

Notably, the beam splitter 103 in FIG. 1A reflects part of each pulse out of the ring cavity and transmits part of each pulse back into the ring cavity each time that pulse travels around the ring cavity. Hence the energy of each pulse diminishes for each round trip traversed inside the ring cavity. In practice, there will be further energy losses at each mirror reflection and each prism face, but these losses will typically be small compared with the fraction of the energy directed out of the cavity by the beam splitter. A sequence of pulses arriving at the beam splitter close together in time can be characterized as providing energy envelopes. In the example embodiment where the optical length of the cavity is approximately half of the distance between input pulses, the energy envelope consists of an even pulse train (i.e. a plurality of even pulses), which arrives at the beam splitter close in time to the arrival of an input pulse, and an odd pulse train (i.e. a plurality of odd pulses), which arrives approximately half way in time between two input pulses. In accordance with one aspect of preferred embodiments of the present invention, these energy envelopes are approximately or substantially equal in energy.

Figure 2A:
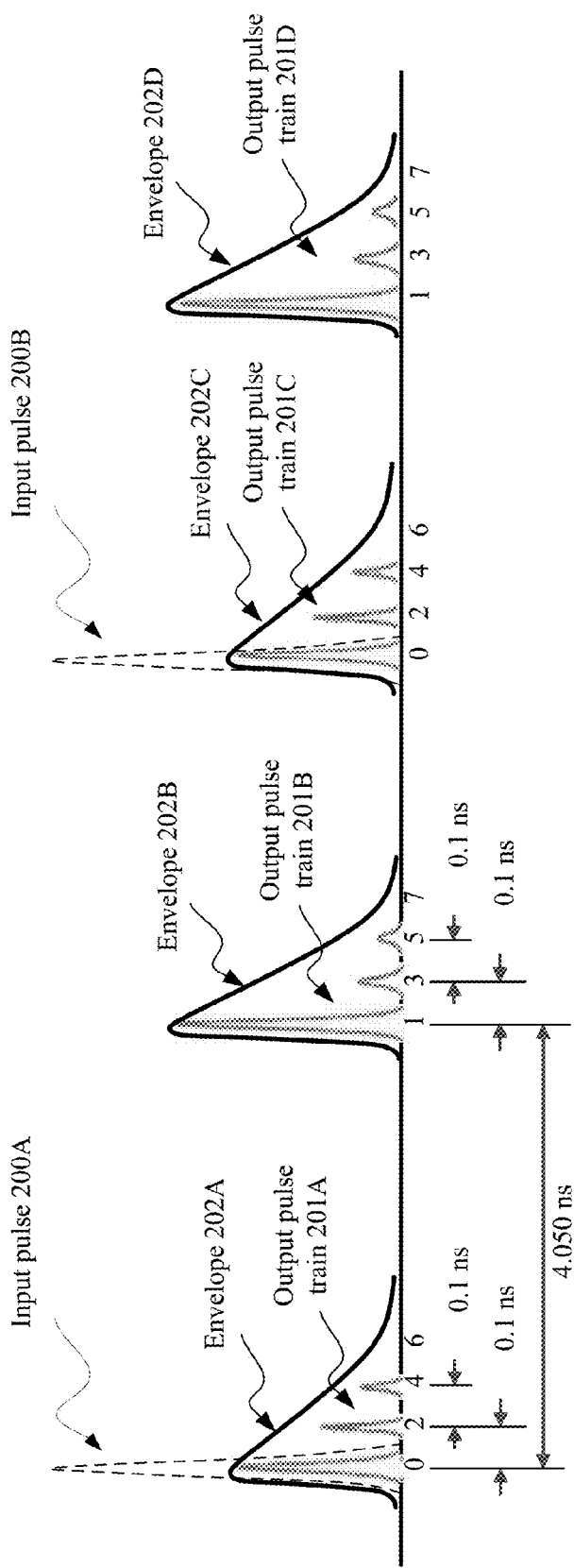
FIG. 2A illustrates exemplary energy envelopes output by one of the pulse multipliers of FIGS. 1A, 1B, 1C, 1D, 1E, 3A, 3B, 4A, and 4B. Each energy envelope includes an output pulse train.

FIG. 2A illustrates exemplary energy envelopes 202A, 202B, 202C, and 202D, which consist of output pulse trains 201A, 201B, 201C, and 201D, respectively. As shown, output pulse trains exemplify the above-described embodiment of a pulse multiplier that doubles the repetition rate of a 125 MHz input. That is, the cavity length is chosen so as to add an extra time delay of approximately 0.05 ns for each round trip, so that the time taken by a single pulse to traverse the entire cavity (i.e. 0→1, 1→2, 2→3 etc.) is 4.050 ns.

Figure 2B:
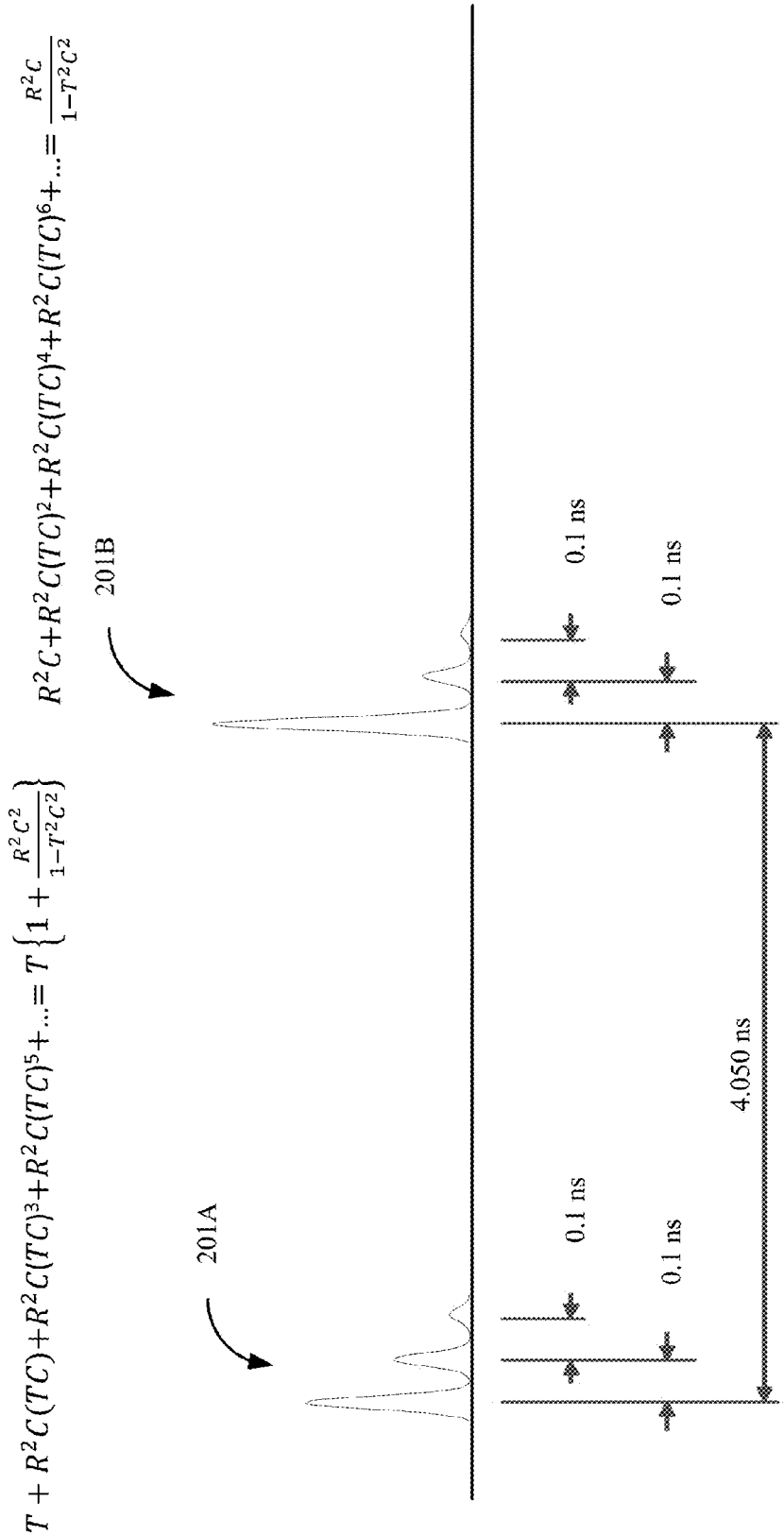
FIG. 2B illustrates that a pulse multiplier can double the original repetition pulse rate while reducing peak power and ensuring substantially equal energy in each pulse.

Note that original pulses 200A and 200B are not part of power envelopes 202A and 200C, but are shown for context. Specifically, beam splitter 103 in FIG. 1A uses original pulses 200A and 200B to generate output pulse trains 201A-201D. The individual pulses under envelopes 202A and 202C are labeled 0, 2, 4, and 6 because the first pulse does not enter the ring cavity and the subsequent pulses have been around the cavity 2, 4, and 6 times. Under envelopes 202B and 202D, the individual pulses are labeled 1, 3, 5, and 7 to indicate the number of times around the cavity for each pulse. FIG. 2B illustrates that the normalized sum of the individual pulses in each of pulse trains 201A and 201B can be made substantially equal to one another, and approximately equal to half of the total energy of each input pulse if the cavity losses from the mirrors and prism are minimal. Thus, the configuration described for pulse multiplier 100 can double the original repetition pulse rate while reducing peak power and ensuring substantially or approximately equal energy in each output pulse.

Notably, referring back to FIG. 1A, during each traversal of the ring cavity, as described above, mirrors 106 and 107 can refocus the light pulses each time they travel around the ring cavity, so that shape or profile of each pulse (as measured, for example, by parameters such as beam waist dimensions, beam waist ellipticity, and $M^2$ (which is an ISO standard well known in the industry, i.e. the ratio of the beam parameter product of an actual beam to that of an ideal Gaussian beam at the same wavelength)) stays approximately constant for, at least, a few round trips. This uniformity allows pulses to be added (for example, as shown in FIGS. 2A and 2B) with minimal differences from envelope to envelope or from beginning to end of one envelope. Note that because each pulse is reduced in energy each time it passes the beam splitter 103, the energy remains significant for only a few round trips. Therefore, small changes in pulse shape or quality, for example caused by optical aberrations such as astigmatism, can be tolerated, because by the time the aberrations have built up to a significant level after multiple round trips, the pulse energy has diminished to a negligible level.

Thus, the beam splitter 103 can generate pulse trains from each input pulse arriving from the direction 101.

If the fraction of energy transmitted by beam splitter 103 is represented by T (also called the transmission T), the fraction reflected by the beam splitter is represented by R (also called the reflectivity R), and the fraction of energy transmitted once around the ring cavity is represented by C (also called the ring-cavity transmission) (defined as the ratio of the energy of one pulse arriving back at the beam splitter to the energy of that same pulse when it initially left the beam splitter), then, for a single input pulse, the output energy of successive pulses will be T, RCR, RC(TC)R, RC(TC)$^2$R, RC(TC)$^3$R, RC(TC)$^4$R, . . . when expressed as fractions of the energy of the input pulse.

Note that conservation of energy implies that T+R≤1 and C≤1. For a lossless beam splitter R+T=1, and for a lossless ring cavity C=1.

If the optical length of the cavity is approximately equal to half of the distance between two successive pulses, then the output envelope 202A in FIG. 2A will comprise a fraction T (labeled 0 underneath this envelope) of the input pulse 200A plus all the pulses that have traversed the ring cavity an even number of times (labeled 2, 4 and 6 under envelope 202A). The envelope 202C will similarly comprise a fraction T of the energy of the input pulse 200B (labeled 0 under envelope 202C), a fraction R$^2$C (TC) of the energy of the pulse 200A that has been around the cavity twice (labeled 2 under the envelope 202C), plus parts of earlier pulses that have been around the ring cavity 4, 6 etc. times. This sum is shown as 201A in FIG. 2B. The output envelopes 202B and 202D in FIG. 2A will each comprise sums of pulses that have traversed the ring cavity odd numbers of times. For example, the pulse labeled 1 under the envelope 202B is the fraction $R^2C$ of the energy of the pulse 200A that has been around the ring cavity once. This sum is shown as 201B in FIG. 2B.

In accordance with one aspect of the pulse multiplier 100, the reflectivity R of the beam splitter, the transmission T of the beam splitter, and the ring cavity transmission C are chosen so that sums 201A and 201B of FIG. 2B are substantially or approximately equal. Those sums will be equal if $R^2C=T+T^2C$.

If the beam splitter loss is represented by $\epsilon_B$, where $\epsilon_B=1-T-R$, and the ring cavity loss is represented by $\epsilon_C$, where $\epsilon_C=1-C$, then for equal pulse envelopes, T is given by the expression:

$$T = \frac{(1-\varepsilon_C)(1-\varepsilon_B)^2}{1+2(1-\varepsilon_C)(1-\varepsilon_B)} \approx \frac{1-\varepsilon_C-2\varepsilon_B}{3-2\varepsilon_C-2\varepsilon_B}$$

The approximate form is useful when $\epsilon_B$ and $\epsilon_C$ are both small compared with 1, which will often be the case. Note that if $\epsilon_B$ and $\epsilon_C$ are both negligible (i.e. neither beam splitter nor cavity losses are significant), then $T=\frac{1}{3}$ and $R=\frac{2}{3}$ for equal pulse envelopes.

Figure 1B:
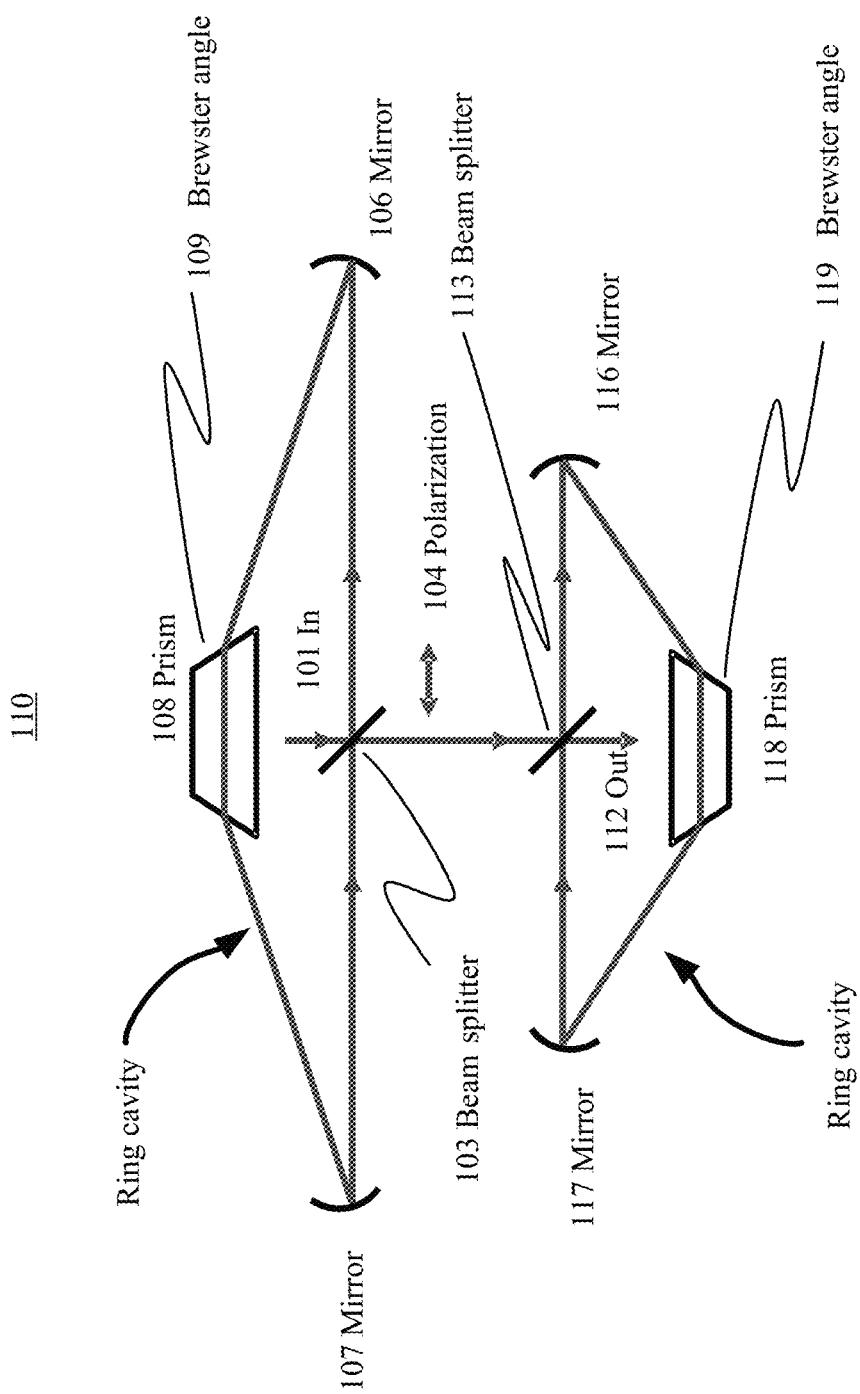
FIG. 1B illustrates an exemplary pulse multiplier configured from two cavities in order to generate a pulse train with a higher repetition rate than can be obtained from a single cavity.

Note that the equations shown in FIG. 2B are for the embodiments of FIGS. 1A and 1B. As explained later, in reference to other embodiments, the roles of T and R are interchanged. For those embodiments, T should be substituted for R, and R for T in the equations as shown in FIG. 2B.

Because T, R, and mirror coatings (and hence $\epsilon_B$ and $\epsilon_C$) may vary slightly from component to component due to normal manufacturing variability, in some applications it may be desirable to be able to make small adjustments to the ring cavity to achieve substantially equal energy in each output pulse. Therefore, in some embodiments, the cavity transmission losses ($\epsilon_C$) can be adjusted in order to substantially match the energies under the odd envelopes (i.e. sum 201B) and even envelopes (i.e. sum 201A). During this adjustment, the prism 108 can be slightly rotated so that light no longer strikes it at precisely Brewster's angle, thereby causing a small fraction of each pulse to be reflected out of the ring cavity and as a result increase $\epsilon_C$. Small adjustments in the angles of the mirrors of the ring cavity can be made as needed to maintain cavity alignment. Because the loss at the prism 108 is at a minimum (substantially zero) when the light is incident on the prism at Brewster's angle, one skilled in the appropriate arts will appreciate that the nominal ring cavity should be for an angle of incidence of the prism slightly displaced from Brewster's angle so that adjustment towards or away from Brewster's angle is possible.

FIGS. 2A and 2B illustrate the case where the ring-cavity length is a little longer (e.g. 50 ps) than half the interval between incoming laser pulses. As shown, the envelopes of each output pulse increase rapidly to a maximum intensity and then decay more slowly as successively weaker pulses arrive at the output. It will be readily appreciated that if the ring-cavity length were slightly shorter (for example, 50 ps shorter) than half the interval between incoming laser pulses, then the envelopes would be substantially reversed in time, slowly building up to a maximum intensity and then decaying more rapidly. The above equations and analysis are applicable for calculating and adjusting the output envelopes. For many applications, either approach would work for doubling the repetition rate and reducing the peak power.

Note that if the cavity length is substantially equivalent to some fraction other than one half of the input pulse separation, for example one third of the pulse separation, then the output pulse envelopes will be determined by different sums from those of FIG. 2B. If the cavity length is substantially equivalent to one third of the pulse separation, then the first envelope will be the sum of the fraction T of the input pulse, plus pulses that have been around the ring cavity a multiple of three times (3, 6 etc.), the second envelope will be the sum of pulses that have been around the ring cavity once, four times, seven times etc., and the third envelope will be the sum of pulses that have been around the ring cavity twice, five times, eight times etc. For this ring cavity length, the fourth envelope will be substantially similar to the first. Because the pulse that has been around the ring cavity twice is necessarily weaker than the pulse that has been around once (since T must be less than 1 else no significant pulse energy enters the cavity) even if the ring cavity is otherwise lossless (C=1), it is not possible to make the second and third output envelopes even approximately equal. If pulse rate multiplication factors greater than 2 are required, but equal energies in each output pulse are not required, then a single ring cavity may be suitable. If substantially or approximately equal pulse energies are required for a pulse rate multiplication factors greater than 2, then two, or more, pulse multipliers must be coupled to achieve that.

Note that, for simplicity, FIG. 1A illustrates the optical components as if they were all laid out in one plane that also contains the input and output light directions 101 and 102. In actual implementations, the components may be laid out in three dimensions. For example, the mirror 106 may reflect the light striking it in a direction that is at least partly downwards so that the input light from the direction 101 passes above the prism 108. In this configuration, the prism 108 would be oriented so that the light leaving it would travel upwards to the mirror 107.

Note also that the beam splitter 103 need not be placed half way between the two mirrors. In other embodiments, the beam splitter 103 could be placed much closer to one mirror than the other. One skilled in the appropriate arts will understand that many different arrangements of the components are possible.

The pulse multipliers of the '075 application, when configured to refocus each pulse as it circulates in the ring cavity, require more components than the pulse multiplier of FIG. 1A. Furthermore, the pulse multipliers of the '075 application use two different polarization states in the ring cavity. These polarization states may complicate the design of the coatings for each surface particularly at deep UV wavelengths. Fabrication of deep UV beam splitters that work well for both polarization states while tolerating the high peak power levels of the incoming laser pulses may be difficult. Similarly, there may not be robust deep UV anti-reflection coatings for transmission elements in the ring cavity, such wave plates (in the '075 embodiments), lenses, or prisms. Therefore, in one alternative embodiment, the use of Brewster's angles for the faces of the prism 108 means minimal light loss can be achieved without any coating on the prism faces. Moreover, as described in further detail below, alignment of the ring can be simplified with the use of fewer components.

FIG. 1B illustrates an exemplary pulse multiplier 110 that includes two ring cavities to generate a higher multiplication factor than can be obtained from a single ring cavity. For example, the first ring cavity may be configured to produce pulses of substantially equal energy at twice the repetition rate of the input laser. The second ring cavity may be configured to produce pulses of substantially equal energy at twice the repetition rate of the output of the first ring cavity, thereby multiplying the repetition rate of the input laser by four while maintaining substantially equal energy in each output pulse. Any of the configurations and all the methods described above for the first ring cavity can be applied to the second ring cavity.

In FIG. 1B, the first ring cavity includes components 103, 106, 108, and 107 as described above. The second ring cavity, which includes a beam splitter 113, mirrors 116 and 117, and a prism 118, functions in an analogous manner to the first ring cavity except that the second ring cavity multiplies the pulse rate of the output of the first ring cavity rather than that directly of the laser. Light from the beam splitter 103 of the first ring cavity is directed to the beam splitter 113 of the second ring cavity. The beam splitter 113 functions substantially similarly to the beam splitter 103. The mirrors 116 and 117 refocus the laser pulses within the second ring cavity and have radii of curvature (and hence focal lengths) appropriate to the optical path length of the second ring cavity (which, in preferred embodiments, is shorter than the optical path length of the first ring cavity). The prism 118 preferably has its input and output faces cut at substantially or approximately Brewster's angle (its input face is labeled 119). The output light leaves the second ring cavity in a direction 112 and comprises a combination of pulses from the first ring cavity and pulses that have circulated around the second ring cavity.

Figure 1C:
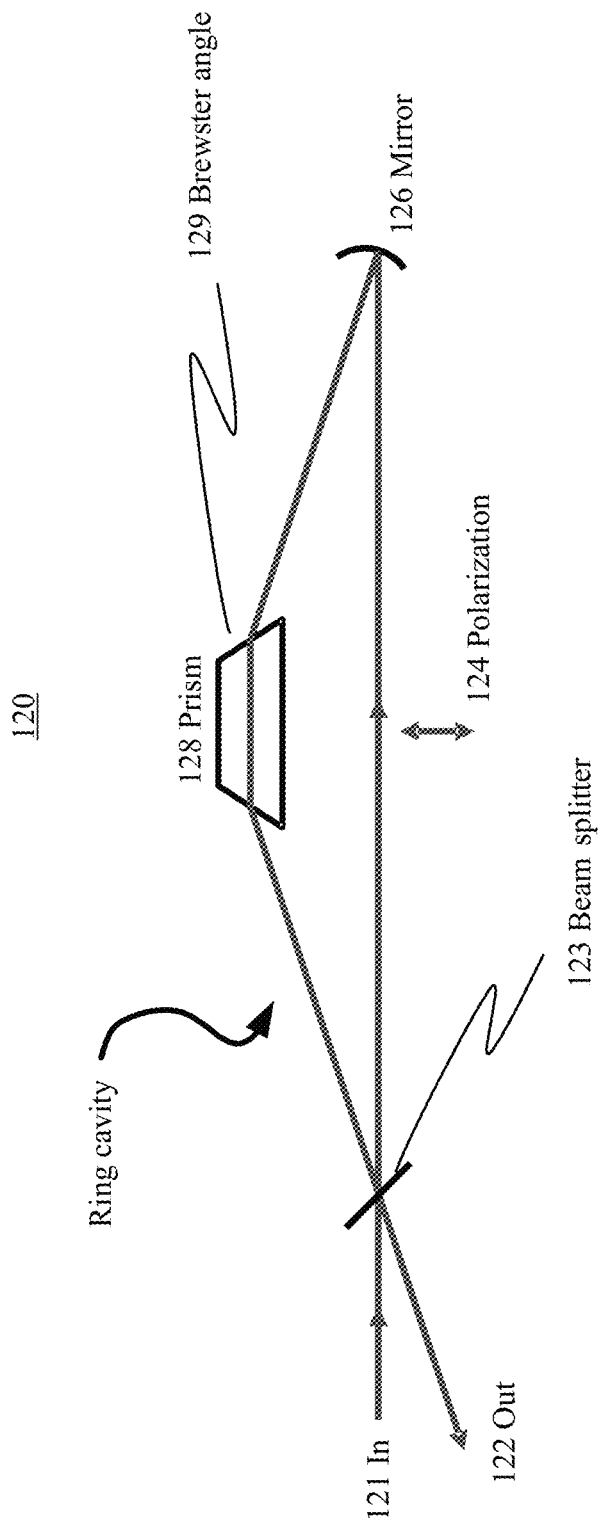
FIG. 1C illustrates an alternative exemplary pulse multiplier configured to generate a pulse trains with a repetition rate that is an integer multiple of the rate of the input pulse train.

FIG. 1C illustrates another exemplary pulse multiplier 120, which uses one mirror rather than the two mirrors (as shown in FIG. 1A). In this embodiment, input light arrives from a direction 121 and is partly reflected by a beam splitter 123 into an output direction 122 (compared with the embodiment of FIG. 1A, where part of the input light is transmitted in the output direction). The light that is transmitted through the beam splitter 123 enters the ring cavity, which includes a mirror 126, a prism 128, and the beam splitter 123. The mirror 126 refocuses the light circulating within the ring cavity. Preferably, the radius of curvature of the mirror 126 is substantially equal to half of the optical path length of the ring cavity so that the beam waist is refocused with a magnification of one each trip around the ring cavity. As in the embodiment of FIG. 1A, Brewster's angle cuts are preferably used for the input and output faces of the prism 128, thereby minimizing or largely eliminating reflection losses at those faces (the input face of prism 128 is labeled 129 in FIG. 1C). In a similar manner to the earlier embodiments, the input light should be substantially or approximately polarized in a direction 124 so as to largely eliminate losses at the prism 128. After light exits the prism 128, it is directed back to the beam splitter 123, where part of each pulse is transmitted through the beam splitter 123 in the output direction 122, and part is reflected back into the ring cavity.

The pulse multiplier 120 functions in a substantially similar manner to the pulse multiplier 100 of FIG. 1A, except that the role of transmission and reflection in the beam splitter 123 of FIG. 1C are interchanged relative to their roles in the beam splitter 103 of FIG. 1A. The above equations can be applied to this ring cavity as long as R and T are interchanged. For substantially equal pulse envelopes when doubling the rate of the input pulses using multiplier 120, R should be approximately ⅓ and T should be approximately ⅔ if the cavity and beam splitter losses are negligible. Slightly different values for R and T can be selected to maintain substantially equal pulse envelopes when there are ring cavity and/or beam splitter losses as taught above for multiplier 100 of FIG. 1A.

One advantage of the pulse multiplier 120 (FIG. 1C) over the pulse multiplier 100 (FIG. 1A) is that pulse multiplier 120 uses one rather than two mirrors resulting in less light loss, especially at deep UV wavelengths. Fewer components can also simplify the optical alignment of the ring cavity. On the other hand, note that optical aberrations, such as astigmatism and lateral color, may be larger for the pulse multiplier 120 (compared to the pulse multiplier 100). Whether these optical aberrations are acceptable depends on the beam waist of the laser, the ring cavity length and the required output pulse beam profile. As one skilled in the appropriate arts will understand, keeping a low angle of incidence on the curved mirror 126 helps minimize optical aberrations.

Figure 1D:
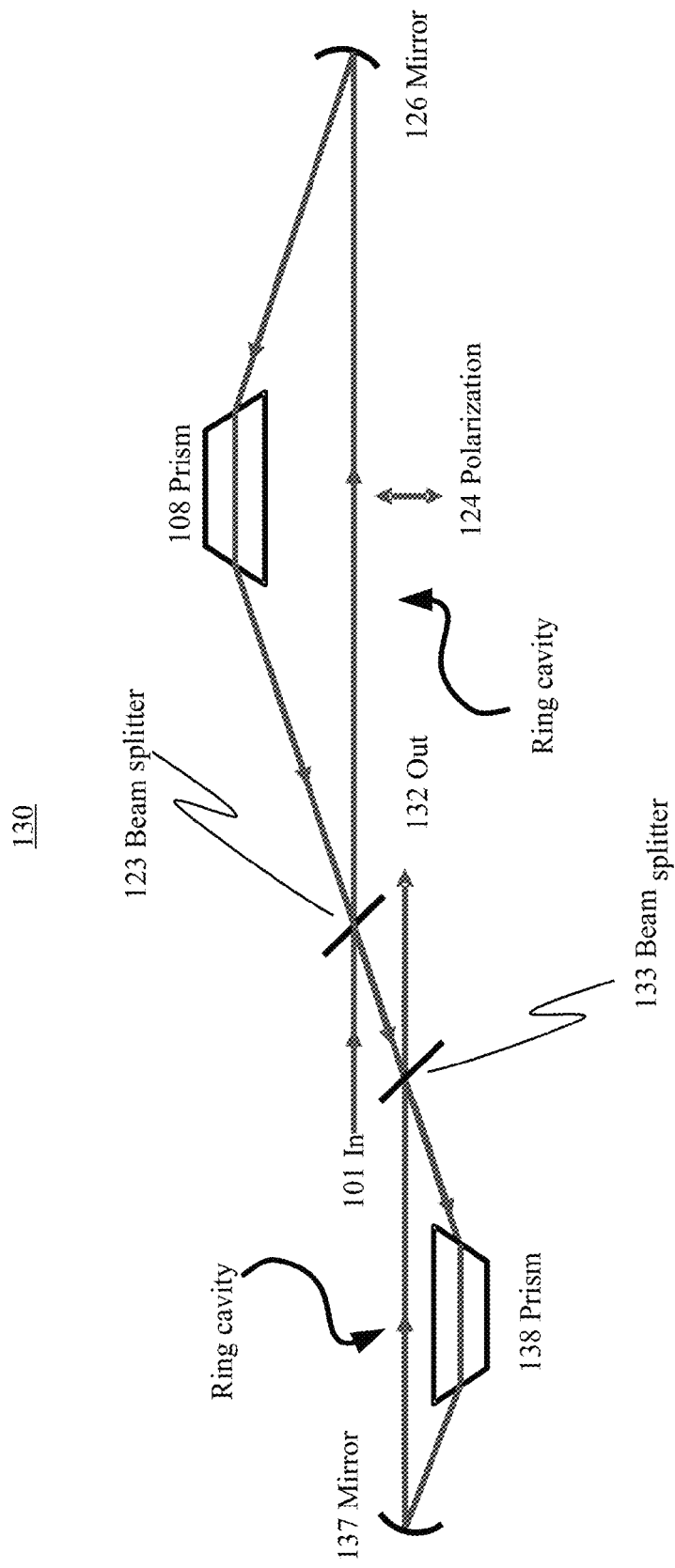
FIG. 1D illustrates one way that two of the cavities shown in FIG. 1C may be coupled in order to generate a pulse train with a higher repetition rate than can be obtained from a single cavity.

FIG. 1D illustrates an alternative exemplary pulse multiplier 130, which includes two ring cavities similar to the one illustrated in FIG. 1C in order to generate a higher multiplication factor than can be conveniently obtained from a single ring cavity. For example, the first ring cavity may be configured to produce pulses of substantially equal energy at twice the repetition rate of the input laser. The second ring cavity may be configured to produce pulses of substantially equal energy at twice the repetition rate of the output of the first ring cavity, thereby multiplying the repetition rate of the input laser by four while maintaining substantially equal energy in each output pulse.

In FIG. 1D, the first ring cavity includes the beam splitter 123, the mirror 126, and the prism 108, as described above. The second ring cavity includes a beam splitter 133, a mirror 137, and a prism 138. Light from the beam splitter 123 of the first ring cavity is directed to the beam splitter 133 of the second ring cavity. The beam splitter 133 functions substantially similarly to the beam splitter 123. The mirror 137 refocuses the laser pulses within the second ring cavity and, preferably, has a radius of curvature substantially equal to half the optical path length of the second ring cavity. As described above for other embodiments, the prism 138 preferably has its input and output faces cut so that the incident and transmitted rays are at substantially or approximately Brewster's angle relative to the face. The output light leaves the second ring cavity through the beam splitter 133 in a direction 132 and comprises a combination of pulses from the first ring cavity and pulses that have circulated around the second ring cavity. The beam splitter 133 also recirculates a fraction of each pulse as described for previous embodiments.

Figure 1E:
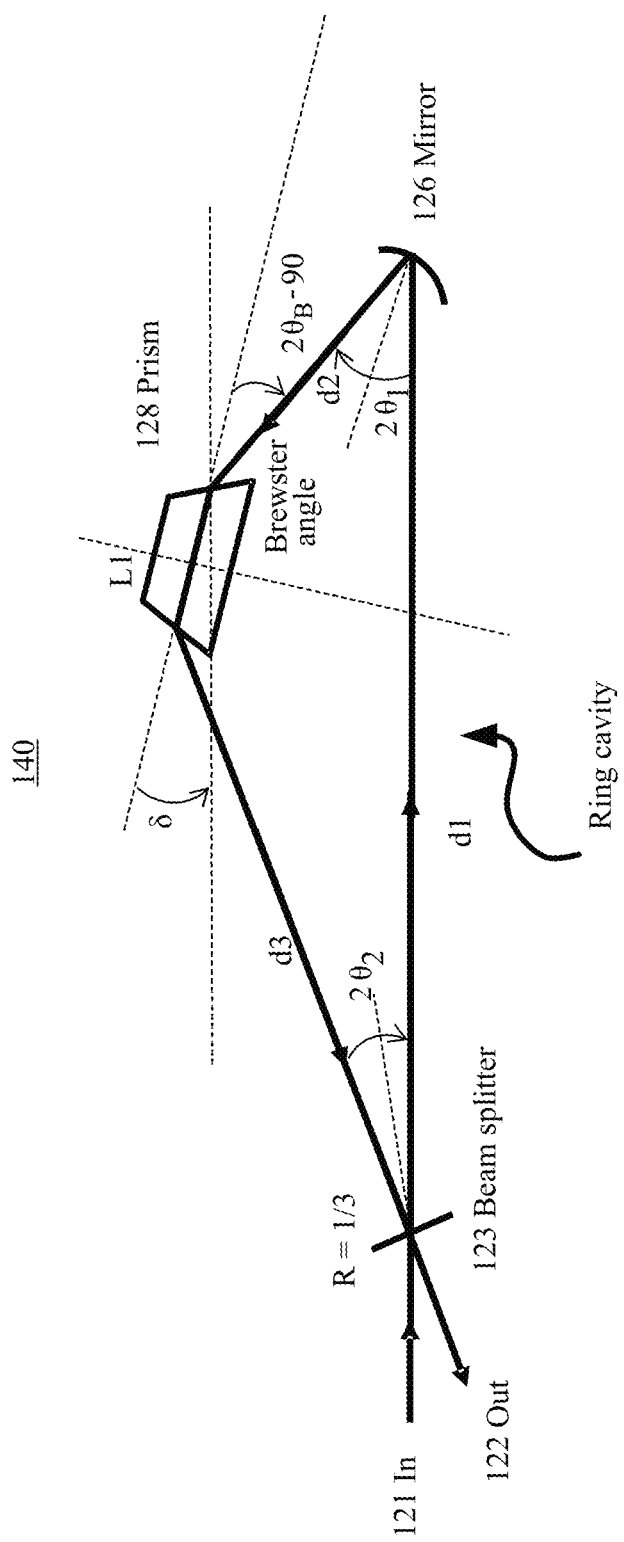
FIG. 1E illustrates more details of one embodiment of the pulse multiplier shown in FIG. 1C.

FIG. 1E shows another exemplary pulse multiplier 140 with a different layout than that of FIG. 1C (but the same components). If the angles of incidence of the light in the ring cavity are substantially similar on the mirror 126 and the beam splitter 123 of FIG. 1C, then keeping those angles of incidence low will result in the optical path length from the mirror 126 through the prism 128 to the beam splitter 123 being only slightly longer than the optical path length from the beam splitter 123 to the mirror 126. Because the mirror 126 preferably has a radius of curvature substantially equal to half the total optical path length of the cavity, the laser pulses will be refocused to a beam waist at a location between the prism 128 and the beam splitter 123, but typically quite close to the beam splitter 123. For pulse multipliers used at deep UV wavelengths, this may result in a high power density incident on the surface of the beam splitter 128 and may degrade its lifetime.

The embodiment of FIG. 1E modifies the geometry of the ring cavity in order to move the beam waist a little further from the surface of the beam splitter 123. In some preferred embodiments, the beam waist is placed approximately half way between the output face of the prism 128 and the surface of the beam splitter 123.

As shown in FIG. 1E, the distance between the beam splitter 123 and the mirror 126 is d1, the distance between the mirror 126 and the input face of the prism 128 is d2, the length of the prism 128 along the axis followed by the light is L1 and the distance from the output face of the prism 128 to the beam splitter 123 is d3. Hence, the total optical path length of the ring cavity is equal to d1+d2+d3+L1*n, where n is the refractive index of the prism material at the wavelength of the laser. For example, if the prism 128 comprises $CaF_2$ and the laser wavelength is 266 nm, then the refractive index would be 1.462. If, for example, the repetition rate of the input laser is 125 MHz and a doubling of the repetition rate is to be performed by the ring cavity, then the optical path length of the ring cavity should be approximately equal to the distance traveled by light in 4 ns, i.e. about 1.199 m. As explained above, in certain preferred embodiments, the optical path length of the ring cavity would be set to a length a little longer, or a little shorter, than this distance in order to further reduce the peak power of the laser. For example, the optical path length of the ring cavity might be set to be approximately 1.214 m for a laser with a repetition rate of 125 MHz.

As explained above, preferably the radius of curvature of the mirror 126 is approximately equal to half the optical path length. The laser beam waist will be refocused half the optical path length away from the mirror 126. The input laser should preferably be focused before the beam splitter 123 so that the optical path distance from the laser beam waist to the mirror 126 is also approximately equal to half the optical path of the cavity.

The angle of incidence on the mirror 126 is $\theta_1$, so that the light incident on the mirror 126 is deflected through an angle of $2\theta_1$, as shown. The angle of incidence on the beam splitter 123 is $\theta_2$. Brewster's angle, $\theta_B$, for the prism 128 is determined by the refractive index of the prism material at the laser wavelength. For $CaF_2$ at a wavelength of 266 nm, Brewster's angle is approximately 55.6°. As shown the ray incident on the face of the prism 128 at Brewster's angle is deviated by an angle equal to $2\theta_B-90°$ (i.e. an angle of about 21.3° for $CaF_2$ at a wavelength of 266 nm). The prism 128 is tilted as shown at an angle δ relative to a line parallel to the light between the beam splitter 123 and the mirror 126.

From geometry, the following relationships can be derived:

$$2\theta_1 = 2\theta_B - 90° + \delta$$

$$2\theta_2 = 2\theta_B - 90° - \delta$$

$$d1 = L1*\cos(\delta) + d2*\cos(2\theta_1) + d3*\cos(2\theta_2)$$

$$d3*\sin(2\theta_2) = d2*\sin(2\theta_1) + L1*\sin(\delta)$$

These equations combined with the desired ring-cavity optical path length and properties of the prism 128, allow selection of the appropriate angles, prism length L1 and component separations d1, d2 and d3 to place the beam waist at a desired location, while maintaining a reasonably small angle of incidence $\theta_1$ on the mirror 126 so to keep optical aberrations acceptable.

In a similar manner to that shown in FIGS. 1B and 1D, two cavities like that shown in FIG. 1E can be included (i.e. optically coupled) to achieve a higher multiplication rate, such as a four times multiplication rate.

Figure 3A:
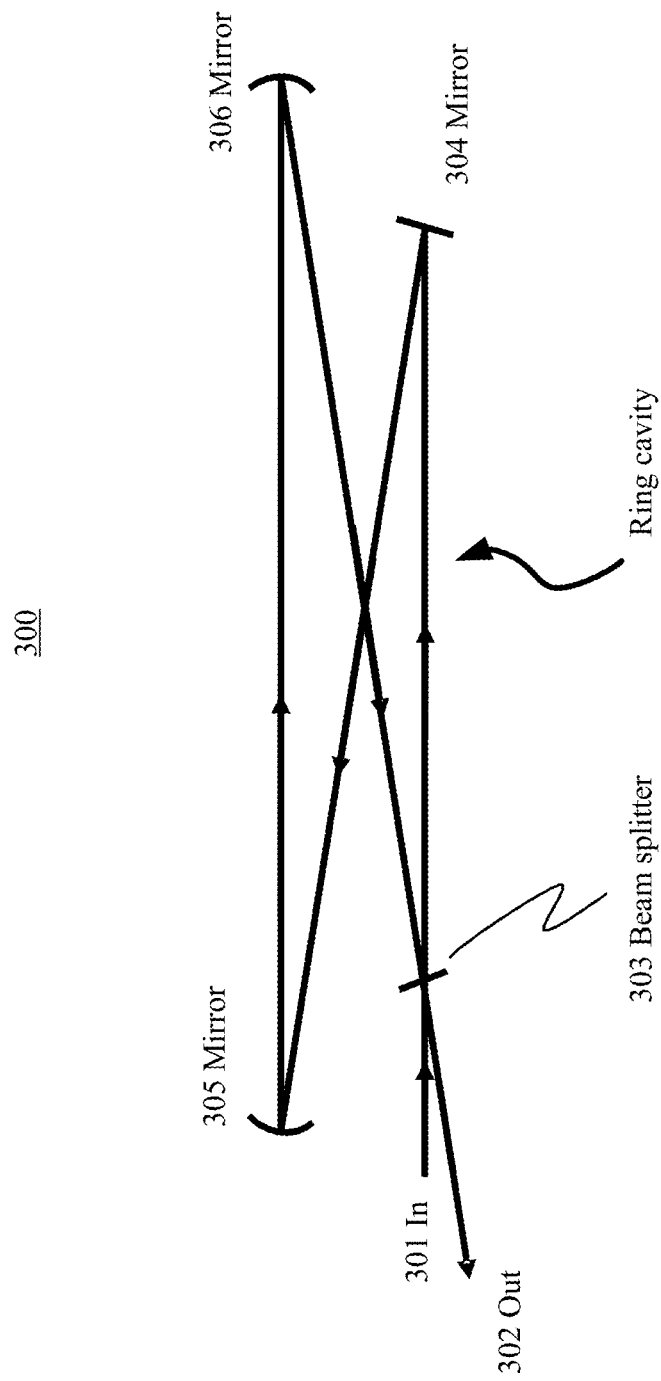
FIGS. 3A and 3B illustrate alternative exemplary pulse multipliers comprising a single butterfly ring cavity and two butterfly ring cavities respectively.

FIG. 3A shows an exemplary laser pulse multiplier 300, which does not include a prism and therefore may be used when there is no readily available and/or inexpensive material for the prism compatible with the laser wavelength and peak power level.

Laser pulses arrive from direction 301. Part of each pulse is reflected from a beam splitter 303 into an output direction 302 and part enters a ring cavity (which may be called a butterfly ring cavity because of its crossing paths). As explained above, if the ring cavity and the beam splitter 303 were lossless, then the beam splitter 303 would preferably reflect about one third of the energy of each laser pulse and transmit about two thirds into the ring cavity. As explained above, these values can be modified to account for beam splitter and ring cavity losses in order to maintain substantially equal energy output pulses in a pulse rate doubler.

After a laser pulse enters the ring cavity, it is reflected from a flat mirror 304 and directed towards a curved mirror 305. The mirror 305 reflects the laser pulse towards a curved mirror 306. The mirror 306 reflects the laser pulse back towards the beam splitter 303. The curvatures of the mirrors 305 and 306 are chosen to refocus each laser pulse inside the ring cavity. Different combinations of radii of curvature, and hence focal lengths, of the mirrors 305 and 306 are possible. For example, the input laser pulses may be focused to a beam waist substantially half way between the beam splitter 303 and the mirror 304. The mirror 305 could have a radius of curvature chosen so as to collimate the laser pulses. The mirror 306 could have the same radius of curvature (assuming a symmetric layout of the components) to refocus the each pulse to a beam waist substantially half way between the beam splitter 303 and the mirror 304. In another embodiment, the input laser pulses are substantially collimated. In this case, the mirror 305 can refocus the laser pulses to a beam waist substantially half way between the mirrors 305 and 306. The mirror 306 then can re-collimate the laser pulses. One skilled in the appropriate arts would understand that other refocusing schemes, in addition to the two described above, are possible.

When the pulse strikes the beam splitter 303, part of the pulse is transmitted in the output direction 302 and part is recirculated around the ring cavity. As explained above, the cavity length may be equivalent to a little greater than, or a little less than, half the interval between two successive incoming laser pulses.

One skilled in the appropriate arts would understand that the flat mirror 304 and one of the curved mirrors 305 and 306 could be swapped in location with an appropriate change in the focal length of the curved mirrors.

Figure 3B:
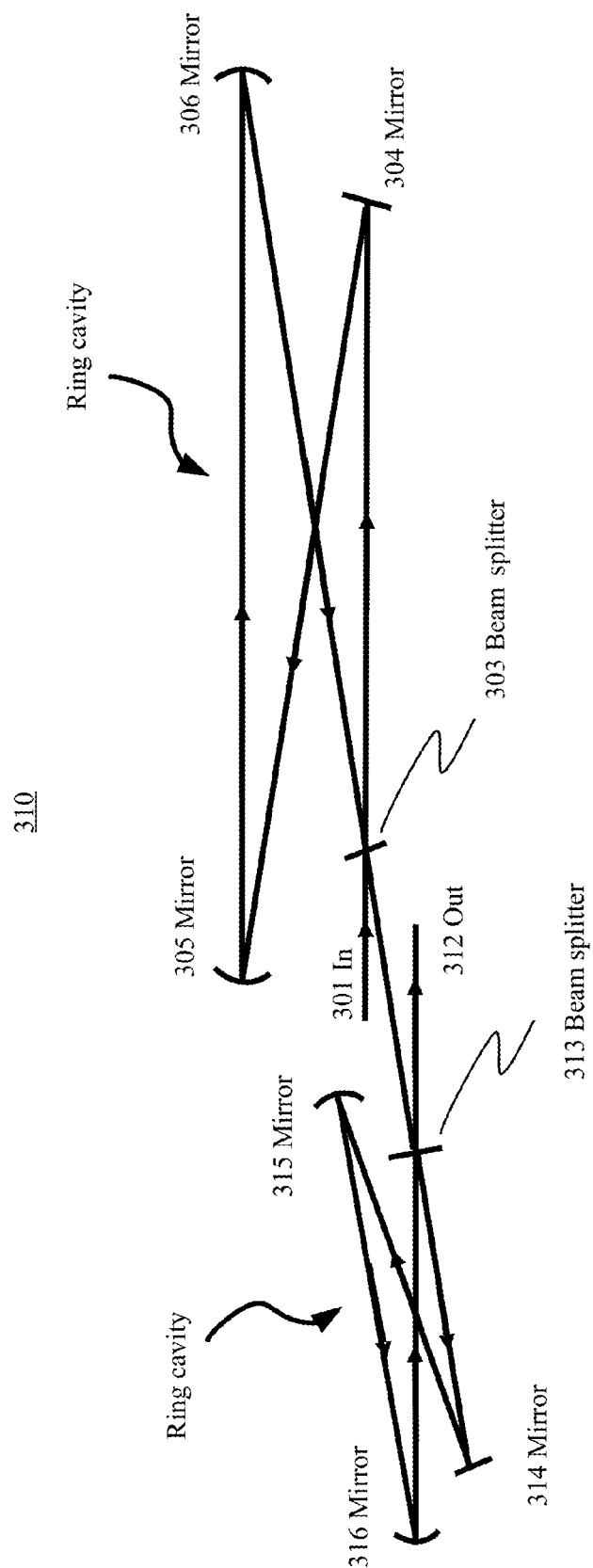

FIG. 3B illustrates an alternative exemplary pulse multiplier 310, which includes two ring cavities similar to the one illustrated in FIG. 3A in order to generate a higher multiplication factor than can be conveniently obtained from a single ring cavity. For example, the first ring cavity may be configured to produce pulses of substantially equal energy at twice the repetition rate of the input laser. The second ring cavity may be configured to produce pulses of substantially equal energy at twice the repetition rate of the output of the first ring cavity, thereby multiplying the repetition rate of the input laser by four while maintaining substantially equal energy in each output pulse.

In FIG. 3B, the first ring cavity includes components 303, 304, 305 and 306 as described above. The second ring cavity comprises a beam splitter 313 and mirrors 314, 315 and 316. Light from the beam splitter 303 of the first ring cavity is directed to the beam splitter 313 of the second ring cavity. The beam splitter 313 functions substantially similarly to beam splitter 303. The mirror 314 redirects the light to the curved mirror 315. The mirrors 315 and 316 refocus the laser pulses within the second ring cavity. The output light leaves the second ring cavity through the beam splitter 313 in a direction 312 and comprises a combination of pulses from the first ring cavity and pulses that have circulated around the second ring cavity. The beam splitter 313 also recirculates a fraction of each pulse as described for previous embodiments.

Note that, although FIG. 3B depicts the components as if they were laid out in one plane, the layout may be three dimensional. For example, the input laser pulses from the direction 101 may travel above or below the optical components of the second ring cavity.

Figure 4A:
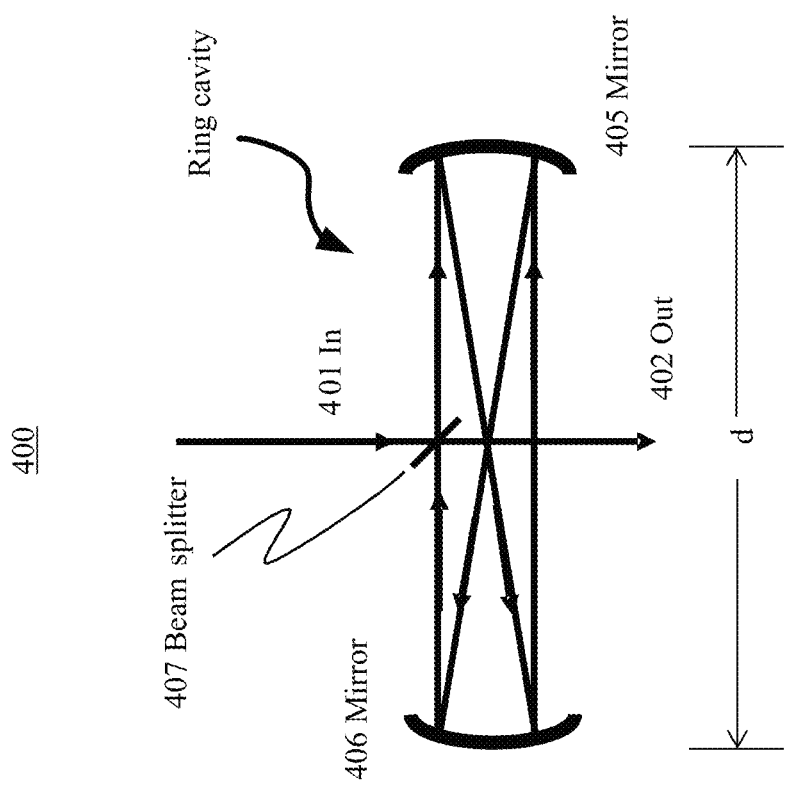
FIG. 4A illustrates an alternative exemplary pulse multiplier based on a Herriott cell.

FIG. 4A shows another exemplary laser pulse multiplier 400, which also does not include a prism. This embodiment includes only a beam splitter and two curved mirrors of substantially equal radius of curvature. Alignment of this embodiment is particularly simple. This embodiment is similar to a Herriott cell as described in Herriott et al., "Off-axis Spherical Mirror Interferometers", Applied Optics 3, #4, pp 523-526 (1964) and Herriott et al., "Folded Optical Delay Lines", Applied Optics 4, #8, pp 883-889 (1965). Notably, this embodiment includes a beam splitter in the ring cavity in order to perform pulse multiplication. The Herriott et al. references do not describe the inclusion of a beam splitter in the cavity and do not describe pulse rate multiplication applications.

Laser pulses arrive from a direction 401. Part of each pulse is transmitted by a beam splitter 407 in an output direction 402 and part enters the ring cavity. As explained above for FIG. 1A, when used as a pulse rate doubler, if the ring cavity and the beam splitter 407 were lossless, then the beam splitter 407 would preferably transmit about one third of the energy of each laser pulse and reflect about two thirds into the ring cavity. As explained above, these values can be modified to account for the beam splitter and cavity losses in order to maintain substantially equal energy output pulses in a pulse rate doubler.

After a laser pulse enters the ring cavity, it is reflected from a curved mirror 405 and directed towards a curved mirror 406. The mirror 406 redirects the light back towards the mirror 405. After multiple reflections from both mirrors (two reflections from each mirror in the example shown in FIG. 4A), the pulse arrives back at the beam splitter 407 after refocusing. As described by Herriott et al. (1964), the number of reflections from each mirror depends only on the radius of curvature of the two mirrors relative to the separation of the mirrors d, and does not depend on the exact angle that the light enters the ring cavity. For example, if the radius of curvature of the two mirrors is d (i.e. the focal length of each mirror is d/2), then after two reflections from each mirror, each pulse will have been refocused and will arrive back at the beam splitter 407, where a part of the pulse will be reflected out of the ring cavity in the direction 402 and part will be transmitted back into the ring cavity. Herriott et al. (1964) gives values for the focal length of the mirrors (and hence radius of curvature) as a multiple of d for 2, 3, 4, 6, 12 and 24 reflections off each mirror. As explained by Herriott et al., other numbers of reflections are possible. As described by Herriott et al. (1964), the reflections may not lie in one plane, depending on the number of reflections and the angle that the light is incident on the mirror 405 from the beam splitter 407. More than two reflections from each mirror make the cavity more compact compared with a cavity using two reflections from each mirror. However since some light is lost at each mirror reflection, two reflections per mirror will be preferred when mirror reflection losses are not so small (as, for example, at deep UV wavelengths), but more than two reflections per mirror may be usable when losses per reflection are small (for example at infra-red, visible or near UV wavelengths).

The pulse multiplier 400 will refocus the laser pulses regardless of the location of the beam waist of the input laser pulses, so that the output pulses leaving in the direction 402 will appear to have approximately or substantially similar divergence and beam waist location as the input pulses. In some preferred embodiments of the pulse multiplier 400, the input laser pulses from the direction 401 will be substantially collimated so as to minimize the power density incident on the beam splitter 407. The output laser pulses will then be substantially collimated also.

Figure 4B:
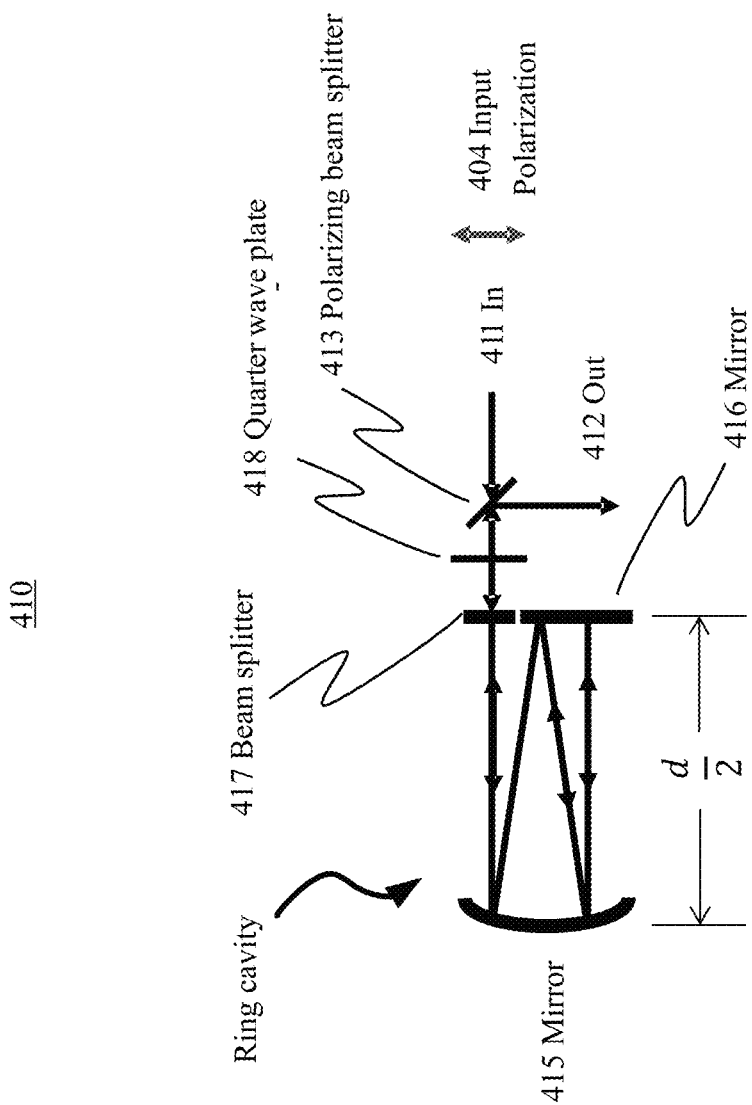
FIG. 4B illustrates an alternative exemplary pulse multiplier based on half of a Herriott cell.

FIG. 4B shows another pulse rate multiplier 410 that is more compact than pulse multiplier 400 of FIG. 4A. The pulse multiplier 410 uses a flat mirror 416 to retro-reflect the light from a curved mirror 415, thus halving the distance between the two mirrors of the multiplier compared with the pulse multiplier 400 for the same cavity optical path length (i.e. a mirror separation of d/2 for the pulse multiplier 410 results in the same optical path length as a mirror separation of d for the pulse multiplier 400). The curved mirror 415 has the same radius of curvature as mirror 405 (FIG. 4A). Another advantage of the pulse multiplier 410 over the pulse multiplier 400 is that the beam splitter 417 can be positioned approximately coplanar with the flat mirror 416, thereby simplifying construction and alignment. Note that the roles of reflection and transmission of the beam splitter 417 are interchanged compared with their roles in the beam splitter 407 in the pulse multiplier 400.

The pulse multiplier 410 uses a second beam splitter 413 to separate input and output laser pulses. In the embodiment shown in FIG. 4B, the beam splitter 413 is a polarizing beam splitter arranged so as to transmit substantially 100% of the incoming laser pulses, which are substantially p polarized relative to the beam splitter 413 as shown by an arrow 404. In certain embodiments, this transmission is achieved by orienting the beam splitter 413 so that light from the direction 411 is incident at approximately Brewster's angle for the wavelength of the laser.

In order that the beam splitter 413 reflects a high percentage of the energy of each output pulse, the polarization of the output pulses needs to be oriented substantially as s polarization relative to the beam splitter 413. This polarization can be achieved by a quarter-wave plate 418 positioned between the beam splitters 413 and 417. The quarter-wave plate 418 is oriented so as to convert the input polarization to substantially circular polarization. After an odd number of reflections inside the ring cavity (seven reflections in the embodiment shown in FIG. 4B), the handedness of the circular polarization has been reversed (i.e. left circular becomes right circular polarization or vice versa), so that output pulses, when they pass the quarter-wave plate 418 are converted back to substantially linear polarization that is rotated 90° relative to the input polarization. Note that the quarter-wave plate 418 is outside the ring cavity in contrast to the embodiments of the '075 application, which contain wave plates in the ring cavity.

None of the embodiments of the pulse multiplier described herein require a wave plate in the ring cavity. Instead, the beam splitter alone is used to determine the fraction of each pulse that leaves the cavity and the fraction that is recirculated around the cavity.

Note that the beam waist in the pulse multiplier 410 may be on, or close to, the surface of the mirror 416. The choice of whether to use the pulse multiplier 410 or the pulse multiplier 400 depends on the wavelength of the laser, the power density, and the space available for the ring cavity.

In a similar manner to the embodiments of FIGS. 1 and 3, two or more pulse multipliers of the embodiments shown in FIGS. 4A and 4B may be coupled together to achieve higher multiplication rates.

Advantageously, inspection systems can include the above-described pulse multipliers. The inspection system can be a bright-field inspection system, a dark-field inspection system, or a system with both bright-field and dark-field modes. The inspection system can be configured to inspect semiconductor wafers or photo-lithography masks. Specifically, the inspection system may be configured to detect patterning defects on a patterned sample, or may be configured to detect particles, pits, or bumps on a patterned or un-patterned surface.

For example, the high-repetition rate laser pulses generated by the above-described pulse multipliers can be used in a flash-on-the-fly inspection system, wherein a single laser pulse illuminates a portion of a moving sample (such as a wafer or reticle) that is to be inspected and an image is acquired by a camera. Because each laser pulse is of short duration, the motion is effectively frozen and an un-blurred image is acquired. Advantageously, a higher repetition rate, as provided by the above-described pulse multipliers, can enable more images to be acquired per unit time, thereby allowing faster motion. In some embodiments of a pulse multiplier used in a flash-on-the-fly inspection system, since one goal is to freeze the motion, it is preferred not to overly broaden each laser pulse when multiplying the pulse rate. Accordingly in such embodiments, the cavity length may be set to be substantially equivalent to one half of the time interval between successive incoming pulses.

Figure 5:
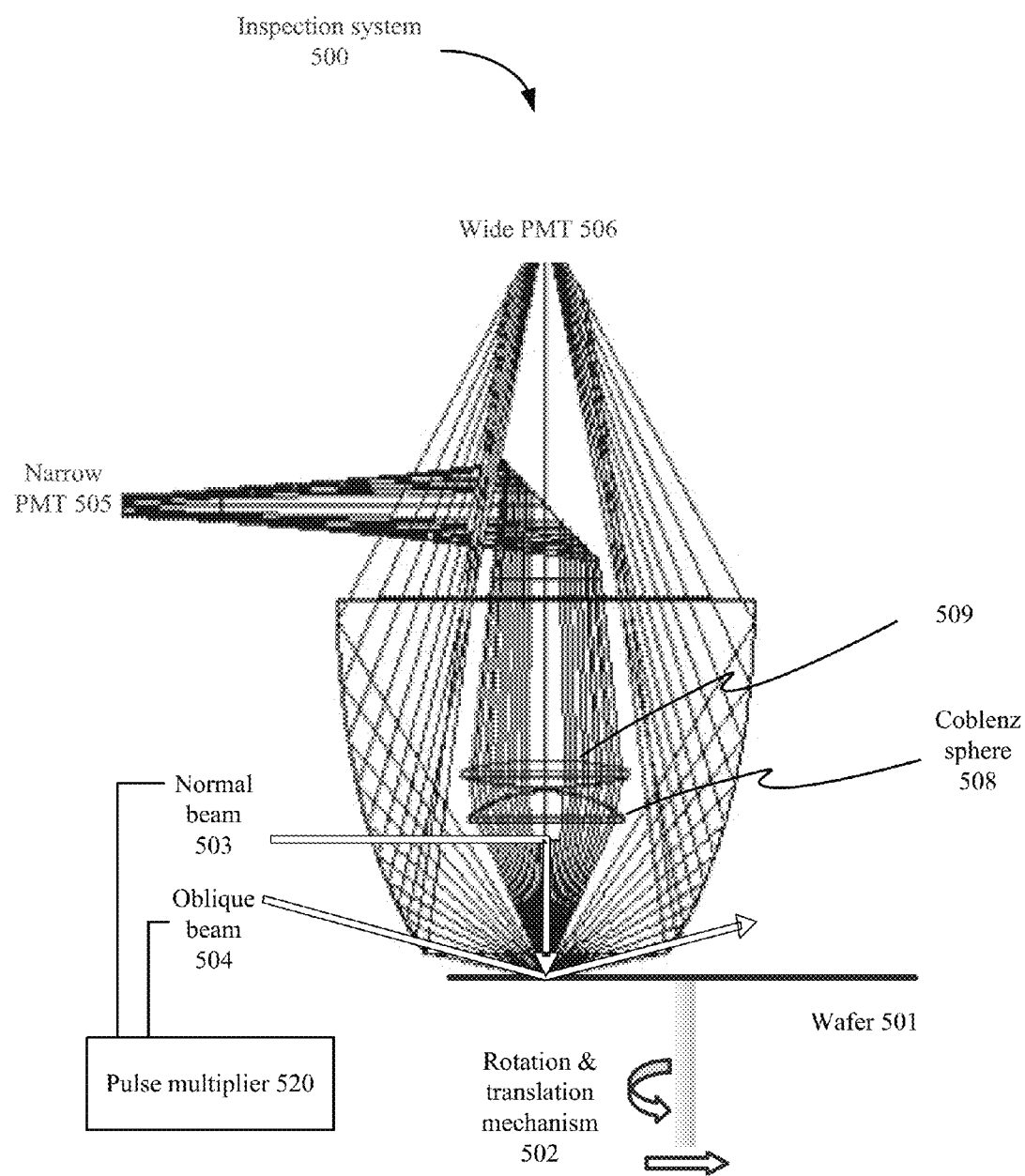
FIG. 5 illustrates an exemplary unpatterned wafer inspection system incorporating a pulse multiplier.

FIG. 5 illustrates an exemplary unpatterned wafer inspection system 500 including a light source that incorporates a pulse multiplier 520. In system 500, a wafer 501 can be rotated and translated using a mechanism 502 to ensure the wafer's whole surface is scannable. The pulse multiplier 520 can advantageously generate pulses for a normal beam 503 and an oblique beam 504 that are directed onto the wafer 501. The reflected incident light from the wafer 501 is then directed, for example using a Coblenz sphere 508 and optics 509, onto detectors (not shown for simplicity). The system 500 can provide both narrow and wide detection paths, e.g. including a narrow photo multiplier tube (PMT) 505 and a wide PMT 506. U.S. Pat. No. 5,189,481, which issued to Jann et al. on Feb. 23, 1993, describes the system 500 in greater detail, and is incorporated by reference herein. Notably, the pulse multiplier 520 can multiply the pulses from a UV, deep UV, or vacuum UV laser. The pulse multiplier 520 can advantageously increase the repetition rate while reducing the peak power of whatever laser is used.

U.S. Pat. No. 6,201,601, which issued to Vaez-Iravani et al. on Mar. 13, 2001 and U.S. Pat. No. 6,271,916, which issued to Marx et al. on Aug. 7, 2001 provide further details on unpatterned wafer inspection systems that can advantageously incorporate any of the pulse multipliers described herein. Both of these patents are incorporated by reference herein.

Figure 6:
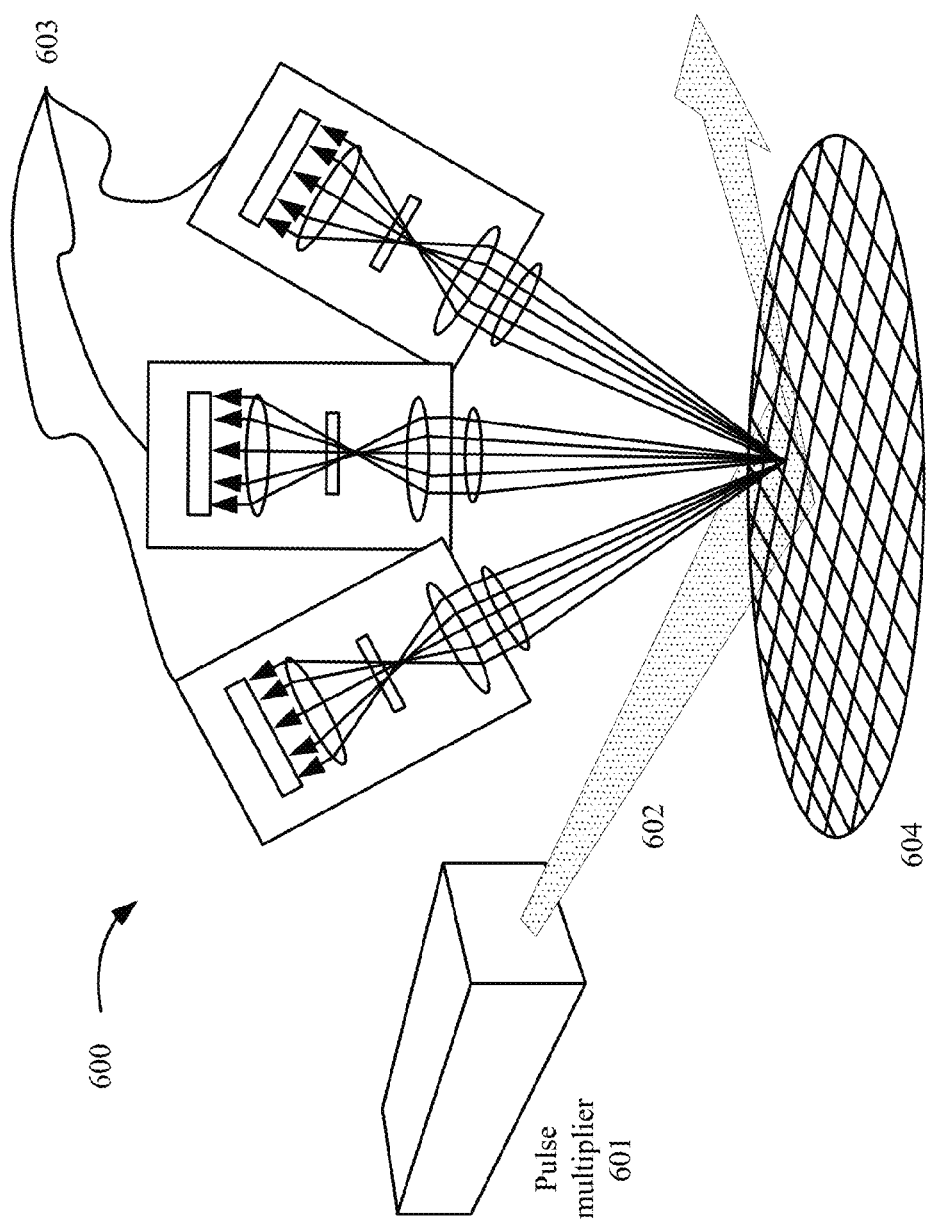
FIG. 6 illustrates an exemplary patterned wafer inspection system incorporating a pulse multiplier.

FIG. 6 illustrates an exemplary patterned wafer inspection system 600 including a light source that comprises a pulse multiplier 601, which can provide both near-normal and oblique illumination (only oblique illumination 602 shown for clarity). The pulse multiplier 601 can generates pulses from a UV, deep UV, or vacuum UV laser. Advantageously, the pulse multiplier 601 can increase the repetition rate of the laser used, while reducing its peak power. In the system 600, multi-channel collection 603 can provide a large collection area, binning, and channel fusion with an increased signal to noise ratio (SNR). Illumination polarization, as generated by the pulse multiplier 601, can provide previous layer suppression and defect selectivity. The illumination channels, which facilitate the multi-channel collection 603, can illuminate one or more spots, one or more narrow lines, or a rectangular area on wafer 604. Detection channels can include Fourier filtering (for pattern suppression), polarization selection, angle range, and/or numerical aperture (NA) control. U.S. Pat. No. 7,525,649, which issued to Leong et al. on Apr. 28, 2009 and is incorporated by reference herein, describes the surface inspection apparatus 600 and other multiple collection systems in further detail.

Advantageously, metrology systems can also include the above-described pulse multipliers. Exemplary metrology systems can include, but are not limited to, an ellipsometer (see, e.g. U.S. Pat. No. 6,734,968, incorporated by reference herein), an angle-resolved reflectometer (see, e.g. U.S. Pat. No. 4,999,014 or U.S. Pat. No. 7,667,841, both incorporated by reference herein) or a photo-acoustic measurement system (see, e.g. U.S. Pat. No. 4,710,030, incorporated by reference herein). In some embodiments of a photo-acoustic measurement system incorporating a pulse multiplier, it is preferred not to overly broaden each laser pulse in order to have a high peak power for each output pulse. Accordingly in such embodiments, the optical length of the cavity may be set to be substantially equivalent to one half of the interval between successive incoming pulses.

Note that any inspection or metrology system including a pulse multiplier can be used in combination with a pulse-shaping and/or coherence-reducing device. Exemplary pulse-shaping and coherence reducing devices include but are not limited to those described in co-pending US Published Patent Applications 2011/0279819 and 2011/0228263 both by Chuang et al. These two applications both claim priority of U.S. Provisional Application 61/100,990 filed Sep. 29, 2008. All of these applications are incorporated by reference herein. Such pulse-shaping devices can be used to reduce the coherence of each laser pulse or otherwise modify the shape of the pulse.

Figure 7:
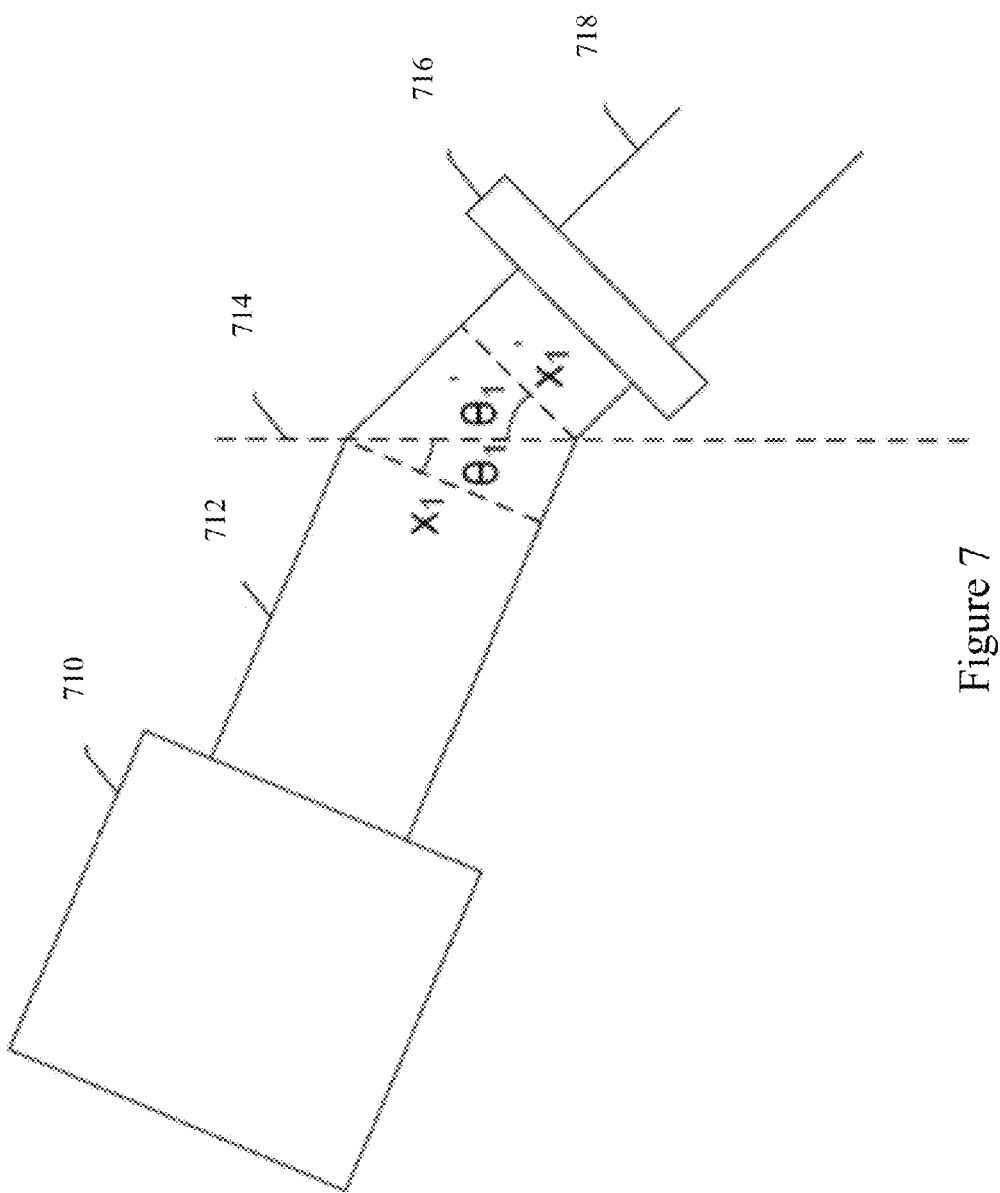
FIG. 7 illustrates an exemplary coherence reducing and/or pulse shaping scheme that may be combined with a pulse multiplier.

FIG. 7 illustrates aspects of a pulse-shaping or coherence reducing device used in conjunction with a pulse multiplier, suitable for incorporation into an inspection or metrology system in accordance with embodiments of the present invention. A light source 710 comprises a pulsed laser and a pulse multiplier. The light source 710 generates a light beam 712 comprising a series of pulses. One aspect of this embodiment is to make use of the finite spectral range of the laser in order to perform a substantially quick temporal modulation of a light beam 712, which can be changed on approximately a tenth picosecond time scales (a tenth picoseconds time interval is equivalent to about 1 pm in spectral width), and transform the temporal modulation to spatial modulation.

The use of a dispersive element and an electro-optic modulator is provided for speckle reduction and/or pulse shaping. For example, the illumination subsystem includes a dispersive element positioned in the path of the coherent pulses of light. As shown in FIG. 7, the dispersive element can be positioned at a plane 714 arranged at angle $\epsilon_1$ to the cross-section $x_1$ of the coherent pulses of light. As further shown in FIG. 7, the pulses of light exit the dispersive element at angle $\theta_1'$ and with cross-sectional dimension $x_1'$. In one embodiment, the dispersive element is a prism. In another embodiment, the dispersive element is a diffraction grating. The dispersive element is configured to reduce coherence of the pulses of light by mixing spatial and temporal characteristics of light distribution in the pulses of light. In particular, a dispersive element such as a prism or diffraction grating provides some mixing between spatial and temporal characteristics of the light distribution in the pulses of light. The dispersive element may include any suitable prism or diffraction grating, which may vary depending on the optical characteristics of the illumination subsystem and the metrology or inspection system.

The illumination subsystem further includes an electro-optic modulator positioned in the path of the pulses of light exiting the dispersive element. For example, as shown in FIG. 7, the illumination subsystem may include an electro-optic modulator 716 positioned in the path of the pulses of light exiting the dispersive element. The electro-optic modulator is configured to reduce the coherence of the pulses of light by temporally modulating the light distribution in the pulses of light. In particular, the electro-optic modulator provides an arbitrary temporal modulation of the light distribution. Therefore, the dispersive element and the electro-optic modulator have a combined effect on the pulses of light generated by the light source. In particular, the combination of the dispersive element with the electro-optic modulator creates an arbitrary temporal modulation and transforms the temporal modulation to an arbitrary spatial modulation of an output beam 718.

In one embodiment, the electro-optic modulator is configured to change the temporal modulation of the light distribution in the pulses of light at tenth picosecond time intervals. In another embodiment, the electro-optic modulator is configured to provide about 1000 aperiodic samples on each period of the modulation of the electro-optic modulator thereby providing a de-coherence time of about $10^{-13}$ seconds.

In accordance with certain embodiments of the present invention an inspection system that incorporates a pulse multiplier may simultaneously detect two channels of data on a single detector. Such an inspection system may be used to inspect a substrate such as a reticle, a photomask or a wafer, and may operate as described in U.S. Pat. No. 7,528,943 which issued to Brown et al. on May 15, 2009. The '943 patent is incorporated by reference herein.

Figure 8:
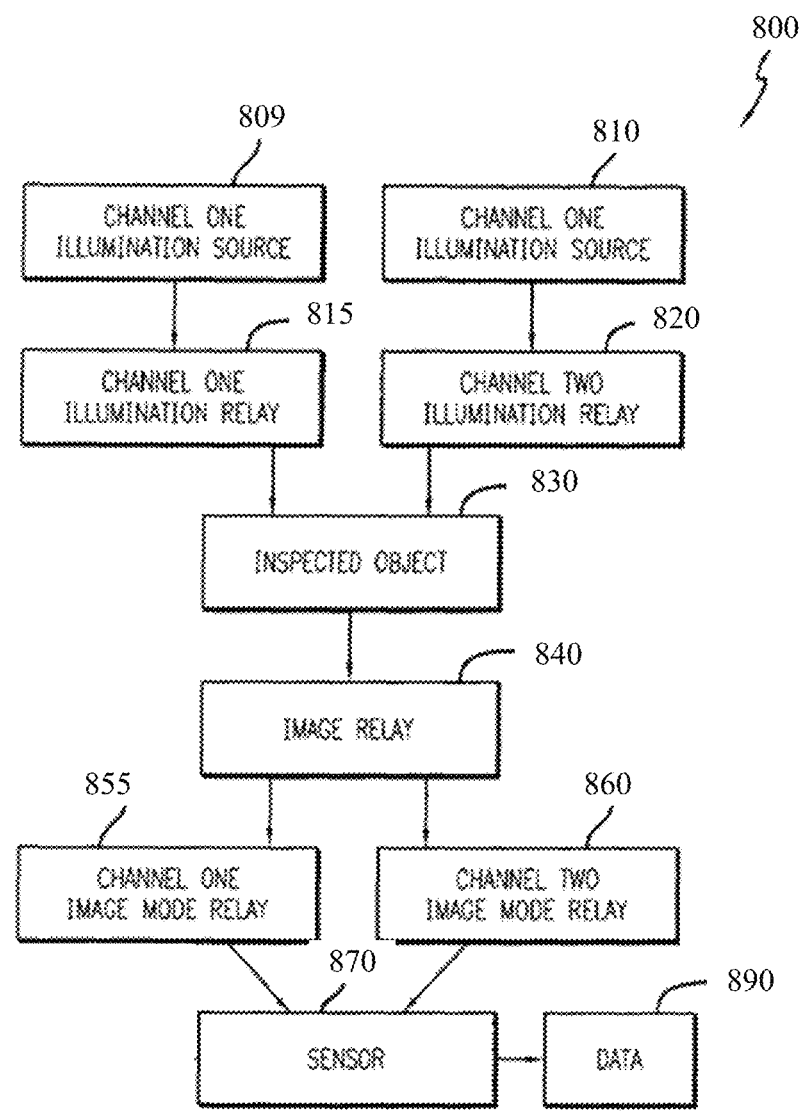
FIG. 8 illustrates an exemplary photomask, reticle or wafer inspection system incorporating a pulse multiplier

FIG. 8 shows a reticle, photomask or wafer inspection system 800 that simultaneously detects two channels of image or signal on one sensor 870. In some embodiments, one or both illumination sources 809 and 810 incorporate a pulse multiplier. In some embodiments, a single light source comprising a pulse multiplier may be used for the illumination sources 809 and 810. The two channels may comprise reflected and transmitted intensity when an inspected object 830 is transparent (for example a reticle or photomask), or may comprise two different illumination modes, such as angles of incidence, polarization states, wavelength or some combination thereof.

As shown in FIG. 8, illumination relay optics 815 and 820 relay the illumination from sources 809 and 810, respectively, to the inspected object 830. The inspected object 830 may be a reticle, a photomask, a semiconductor wafer or other article to be inspected. Image relay optics 855 and 860 relay the light that is reflected and/or transmitted by the inspected object 830 to the sensor 870. The data corresponding to the detected signals or images for the two channels is shown as data 890 and is transmitted to a computer (not shown) for processing.

Other details of reticle and photomask inspection systems and methods that may be configured to measure transmitted and reflected light from the reticle or photomask are described in U.S. Pat. No. 7,352,457 to Kvamme et al, which issued Apr. 1, 2008 and which is incorporated by reference herein. Additional details on reticle and photomask inspection systems and methods that may incorporate a pulse multiplier can be found in U.S. Pat. No. 5,563,702 to Emery et al, which issued Oct. 8, 1996 and which is incorporated by reference herein.

An inspection system incorporating a pulse multiplier in accordance with certain embodiments of the present invention may incorporate multiple channels, where each channel may comprise light having different characteristics (such as type, wavelength range etc.). Inspection systems and methods utilizing multiple channels and suitable for incorporation of a pulse multiplier are described in US Published Application 2009/0180176 to Armstrong et al., which published Jul. 16, 2009 and which is incorporated by reference herein.

An inspection system incorporating a pulse multiplier in accordance with certain embodiments of the present invention may incorporate a primary illumination source, a secondary illumination source and a catadioptric objective, wherein at least one of the illumination sources comprises a pulse multiplier. Inspection systems and methods that are suitable for incorporation of a pulse multiplier, and which utilize primary and a secondary illumination sources and a catadioptric objective are described in US Published Application 2007/0002465 to Chuang et al., which published Jan. 4, 2007 and which is incorporated by reference herein.

Notably, the pulse multiplier can inexpensively reduce the peak power per pulse while increasing the number of pulses per second with minimal total power loss. The pulse multiplier can advantageously enable high speed inspection and metrology with off-the-shelf lasers. Dark-field inspection systems rely on laser light sources. The above-described pulse multiplier allows those systems to use lasers that would otherwise have too low a pulse repetition rate and provides a potential alternative to extremely high repetition rate UV lasers or CW lasers if no appropriate laser is available, or available lasers are too expensive or unreliable.

A detailed description of one or more embodiments of the invention is provided above along with accompanying figures that illustrate the principles of the invention. The invention is described in connection with such embodiments, but the invention is not limited to any embodiment.

For example, in one embodiment, the optical components can be coated with appropriate coatings for the laser wavelength. Each surface of any transmissive elements, such as wave-plates, can also have an anti-reflection coating that minimizes the amount of laser energy reflected at each surface. Mirrors can be coated with coatings designed to maximize the reflection and minimize scattering at the laser wavelength.

In another example, in one embodiment, the ring cavity may have a different shape or a different number of mirrors from the examples given above. For example a White cell (J. White, "Long Optical Paths of Large Aperture", Journal of the Optical Society of America 32 #5, p 285, 1942) or other ring cavity could be used.

In some embodiments, one or more mirrors may be shared between multiple ring cavities. In some cases, this may simplify the alignment as well as making a more compact pulse multiplier compared with separate cavities.

The scope of the invention is limited only by the claims and the invention encompasses numerous alternatives, modifications and equivalents. Numerous specific details are set forth in the above description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

The invention claimed is:

1. A pulse multiplier comprising:
a first ring cavity including:
a first beam splitter that receives a plurality of successive input laser pulses at a first frequency; and
a set of one or more mirrors; and
a second ring cavity including:
a second beam splitter; and
a second set of one or more mirrors;
wherein the first beam splitter directs a first fraction of each of the input laser pulses to the second beam splitter, and directs a second fraction of each of the input laser pulses into the first ring cavity as a first circulated laser pulse,
wherein the second beam splitter directs a third fraction of each laser pulse incident on it to an output of the pulse multiplier, and directs a fourth fraction of energy of each laser pulse incident on it into the second ring cavity as a second circulated laser pulse, and
wherein the first ring cavity has an optical path length of about half the distance between the successive incoming laser pulses, wherein the distance between the successive incoming laser pulses is equal to the velocity of light multiplied by the time interval between the successive incoming laser pulses, and
wherein an optical path length of the second ring cavity is approximately an odd integer times half the optical path length of the first ring cavity.

2. The pulse multiplier of claim 1, wherein the first beam splitter further directs substantially the second fraction of the energy of the first circulated laser pulse out of the first ring cavity to the second beam splitter after the first circulated laser pulse has traversed the first ring cavity once, while directing substantially the first fraction of the energy of the first circulated laser pulse back into the first ring cavity.

3. The pulse multiplier of claim 1, wherein the second beam splitter further directs substantially the fourth fraction of the energy of the second circulated laser pulse out of the second ring cavity as an output of the pulse multiplier after the second circulated laser pulse has traversed the second ring cavity once, while directing substantially the third fraction of the energy of the second circulated laser pulse back into the second ring cavity.

4. The pulse multiplier of claim 1, wherein the first fraction is substantially equal to the third fraction.

5. The pulse multiplier of claim 1, wherein the second fraction is substantially equal to the fourth fraction.

6. The pulse multiplier of claim 1, wherein at least one of the first ring cavity and the second ring cavity is further characterized in that it does not contain a wave plate.

7. The pulse multiplier of claim 1, wherein neither the first ring cavity nor the second ring cavity contains a wave plate.

8. The pulse multiplier of claim 1, wherein the first fraction is approximately one third and the second fraction is approximately two thirds.

9. The pulse multiplier of claim 1, wherein the third fraction is approximately one third and the fourth fraction is approximately two thirds.

10. The pulse multiplier of claim 1, wherein the first fraction, the second fraction, the third fraction and the fourth fraction are chosen so that substantially equal energy output pulses are provided at the output of the pulse multiplier in response to the successive input laser pulses.

11. The pulse multiplier of claim 1, wherein each laser pulse in the first ring cavity is substantially refocused each time that the laser pulse traverses the first ring cavity, and wherein each laser pulse in the second ring cavity is substantially refocused each time that the laser pulse traverses the second ring cavity.

12. The pulse multiplier of claim 1, wherein the first ring cavity further comprises a prism.

13. A pulse multiplier comprising:
a first ring cavity including:
a first beam splitter that receives a plurality of successive input laser pulses;
a prism; and
one and only one mirror, which is a curved mirror; and
a second ring cavity including:
a second beam splitter; and
a second set of one or more mirrors;
wherein the first beam splitter directs a first fraction of each of the input laser pulses to the second beam splitter, and directs a second fraction of each of the input laser pulses into the first ring cavity,
wherein the second beam splitter directs a third fraction of each laser pulse incident on it to an output of the pulse multiplier, and directs a fourth fraction of energy of each laser pulse incident on it into the second ring cavity.

14. The pulse multiplier of claim 1, wherein the second ring cavity further comprises a prism.

15. A pulse multiplier comprising:
a first ring cavity including:
a first beam splitter that receives a plurality of successive input laser pulses;
a set of one or more mirrors; and
a second ring cavity including:
a second beam splitter;
a prism; and
one and only one mirror, which is a curved mirror;
wherein the first beam splitter directs a first fraction of each of the input laser pulses to the second beam splitter, and directs a second fraction of each of the input laser pulses into the first ring cavity,
wherein the second beam splitter directs a third fraction of each laser pulse incident on it to an output of the pulse multiplier, and directs a fourth fraction of energy of each laser pulse incident on it into the second ring cavity.

16. The pulse multiplier of claim 1, wherein said set of one or more mirrors comprise at least two curved mirrors.

17. The pulse multiplier of claim 16, wherein said second set of one or more mirrors comprise at least two curved mirrors.

18. The pulse multiplier of claim 16, wherein at least two of the curved mirrors have substantially similar radii of curvature.

19. A pulse multiplier comprising:
a first ring cavity comprising a Herriott cell or a White cell, the first ring cavity including:
   a first beam splitter that receives a plurality of successive input laser pulses at a first frequency; and
   a set of mirrors including at least two curved mirrors having substantially similar radii of curvature; and
a second ring cavity including:
   a second beam splitter; and
   a second set of one or more mirrors;
   wherein the first beam splitter directs a first fraction of each of the input laser pulses to the second beam splitter, and directs a second fraction of each of the input laser pulses into the first ring cavity,
   wherein the second beam splitter directs a third fraction of each laser pulse incident on it to an output of the pulse multiplier, and directs a fourth fraction of energy of each laser pulse incident on it into the second ring cavity.

20. The pulse multiplier of claim 19, wherein the second ring cavity comprises a Herriott cell or a White cell.

21. A pulse multiplier comprising:
a first ring cavity including:
   a first beam splitter that receives a plurality of successive input laser pulses at a first frequency; and
   a set of one or more mirrors; and
a second ring cavity comprising a Herriott cell or a White cell, the second ring cavity including:
a second beam splitter; and
a second set of mirrors comprising at least two curved mirrors having substantially similar radii of curvature; and
wherein the first beam splitter directs a first fraction of each of the input laser pulses to the second beam splitter, and directs a second fraction of each of the input laser pulses into the first ring cavity,
wherein the second beam splitter directs a third fraction of each laser pulse incident on it to an output of the pulse multiplier, and directs a fourth fraction of energy of each laser pulse incident on it into the second ring cavity.

* * * * *